US008789587B2

(12) United States Patent
Tubel et al.

(10) Patent No.: US 8,789,587 B2
(45) Date of Patent: Jul. 29, 2014

(54) MONITORING OF DOWNHOLE PARAMETERS AND TOOLS UTILIZING FIBER OPTICS

(75) Inventors: Paulo Tubel, The Woodlands, TX (US); Brian Bidigare, Kingwood, TX (US); Michael Johnson, Flower Mound, TX (US); John Harrell, Waxahachie, TX (US); Benn Voll, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 181 days.

(21) Appl. No.: 12/394,395

(22) Filed: Feb. 27, 2009

(65) Prior Publication Data

US 2009/0188665 A1 Jul. 30, 2009

Related U.S. Application Data

(62) Division of application No. 10/447,855, filed on May 29, 2003, now abandoned, which is a division of application No. 09/872,591, filed on Jun. 1, 2001, now Pat. No. 6,588,266, and a division of application No. 09/070,953, filed on May 1, 1998, now Pat. No. 6,268,911, said application No. 09/872,591 is a division of application No. 09/070,953, filed on May 1, 1998, now Pat. No. 6,268,911.

(60) Provisional application No. 60/045,354, filed on May 2, 1997, provisional application No. 60/048,989, filed on Jun. 9, 1997, provisional application No. 60/052,042, filed on Jul. 9, 1997, provisional application No. 60/062,953, filed on Oct. 10, 1997, provisional application No. 60/073,425, filed on Feb. 2, 1998, provisional application No. 60/079,446, filed on Mar. 26, 1998.

(51) Int. Cl.
*E21B 43/12* (2006.01)

(52) U.S. Cl.
USPC .................. 166/250.15; 166/268; 166/252.1; 166/266

(58) Field of Classification Search
USPC ................... 166/261, 270.1, 250.02, 250.05, 166/250.08, 250.15, 66, 266, 268, 252.1, 166/272.2, 271; 73/152.02, 152.12, 152.18, 73/152.24, 152.01
See application file for complete search history.

(56) References Cited

U.S. PATENT DOCUMENTS

| 3,722,605 A | 3/1973 | Isham |
| 3,857,449 A | 12/1974 | Kimura |

(Continued)

FOREIGN PATENT DOCUMENTS

| EP | 050276 A1 | 5/1989 |
| FR | 505276 A | 7/1920 |

(Continued)

OTHER PUBLICATIONS

F. Pigeon et al.; "A vibration sensor, using telecommunication grade monomode fiber, immune to temperature variations," J. Phys. III France 3 (1993), No. 9, XP 000394438, Sep. 1993, pp. 1835-1838.

(Continued)

*Primary Examiner* — Jennifer H Gay
*Assistant Examiner* — Kipp Wallace
(74) *Attorney, Agent, or Firm* — Cantor Colburn LLP

(57) ABSTRACT

A method and system for monitoring and controlling an injection operation is disclosed. A plurality of distributed fiber optic sensors is located in a production well. Fluid is injected into an injection well spaced apart from the production well. A parameter of a formation between the production well and the injection well is determined from measurements from the formation obtained using the fiber optic sensors. At least one of an injection of fluid into the injection well and a flow into the production well is controlled in response to the determined parameter.

14 Claims, 14 Drawing Sheets

(56) References Cited

U.S. PATENT DOCUMENTS

| | | | |
|---|---|---|---|
| 4,279,299 A * | 7/1981 | Shuck | 166/60 |
| 4,344,484 A * | 8/1982 | Ridley | 166/250.15 |
| 4,434,654 A | 3/1984 | Hulsing, II et al. | |
| 4,436,148 A | 3/1984 | Maxwell | |
| 4,485,563 A | 12/1984 | Sharp et al. | |
| 4,488,598 A | 12/1984 | Duerksen | |
| 4,582,131 A | 4/1986 | Plummer et al. | |
| 4,635,723 A | 1/1987 | Spivey | |
| 4,656,743 A | 4/1987 | Thiemann et al. | |
| 4,665,981 A | 5/1987 | Hayatdavoudi | |
| 4,676,313 A * | 6/1987 | Rinaldi | 166/252.1 |
| 4,697,078 A | 9/1987 | Randall | |
| 4,714,564 A | 12/1987 | Lynch et al. | |
| 4,775,009 A * | 10/1988 | Wittrisch et al. | 166/250.11 |
| 4,834,493 A | 5/1989 | Cahill et al. | |
| 4,849,753 A | 7/1989 | Merry | |
| 4,905,774 A | 3/1990 | Wittrisch | |
| 4,994,671 A | 2/1991 | Safinya et al. | |
| 5,131,477 A | 7/1992 | Stagg et al. | |
| 5,144,590 A | 9/1992 | Chon | |
| 5,166,747 A | 11/1992 | Schroeder et al. | |
| 5,331,156 A | 7/1994 | Hines et al. | |
| 5,351,532 A | 10/1994 | Hager | |
| 5,353,237 A | 10/1994 | Bass et al. | |
| 5,361,854 A | 11/1994 | Tull et al. | |
| 5,363,094 A * | 11/1994 | Staron et al. | 340/854.6 |
| 5,363,095 A | 11/1994 | Normann et al. | |
| 5,377,104 A * | 12/1994 | Sorrells et al. | 702/11 |
| 5,379,103 A | 1/1995 | Zigler | |
| 5,418,614 A | 5/1995 | Brost et al. | |
| 5,435,176 A | 7/1995 | Manchak, III | |
| 5,435,969 A | 7/1995 | Hoots et al. | |
| 5,439,054 A * | 8/1995 | Chaback et al. | 166/252.1 |
| 5,455,516 A | 10/1995 | Jean et al. | |
| 5,489,988 A | 2/1996 | Ackley et al. | |
| 5,499,313 A | 3/1996 | Kleinerman | |
| 5,503,225 A | 4/1996 | Withers | |
| 5,515,459 A | 5/1996 | Farhadiroushan | |
| 5,517,024 A | 5/1996 | Mullins et al. | |
| 5,524,709 A * | 6/1996 | Withers | 166/250.1 |
| 5,528,824 A | 6/1996 | Anthony et al. | |
| 5,585,555 A * | 12/1996 | McRae | 73/152.17 |
| 5,596,196 A | 1/1997 | Cooper et al. | |
| 5,597,042 A | 1/1997 | Tubel et al. | |
| 5,662,165 A | 9/1997 | Tubel et al. | |
| 5,684,580 A | 11/1997 | Cooper et al. | |
| 5,717,209 A | 2/1998 | Bigman et al. | |
| 5,729,013 A | 3/1998 | Bergren, III | |
| 5,774,603 A | 6/1998 | Moore et al. | |
| 5,822,058 A | 10/1998 | Adler-Golden et al. | |
| 5,859,430 A | 1/1999 | Mullins et al. | |
| 5,892,860 A * | 4/1999 | Maron et al. | 385/12 |
| 5,926,437 A * | 7/1999 | Ortiz | 367/35 |
| 5,992,519 A * | 11/1999 | Ramakrishnan et al. | 166/250.15 |
| 6,012,016 A | 1/2000 | Bilden et al. | |
| 6,048,175 A | 4/2000 | Corlew et al. | |
| 6,072,567 A * | 6/2000 | Sapack | 356/32 |
| 6,309,597 B1 | 10/2001 | Ballinger, Jr. et al. | |

FOREIGN PATENT DOCUMENTS

| | | |
|---|---|---|
| GB | 2305196 A | 4/1997 |
| JP | 8248107 | 9/1996 |
| WO | WO8101168 | 4/1981 |
| WO | WO9609561 | 3/1996 |
| WO | WO9624748 A | 8/1996 |
| WO | WO9609461 | 3/2006 |

OTHER PUBLICATIONS

Initiatives Online, vol. 3, Feb. 1996, XP-002073713, "The FlowProbe performs chemical analysis in real-time," pp. 1-2.

O. S. Karaman et al.; "A Field Trial to Test Fiber Optic Sensors for Downhole Temperature and Pressure Measurements," West Coalinga Field, California, XP-002082002, SPE 35685, Society of Petroleum Engineers, Western Regional Meeting, Anchorage, Alaska, May 22-24, 1996, pp. 351-357.

S. Heath; "On-Line Chemical Sensing Technology for Downhole and Topside Monitoring of Produced Brines," XP-002082001, Nov. 20, 1995, pp. 1-19.

G. Botto et al.; "Electronic Fiber-Optic Technology: Future Options for Permanent Reservoir Monitoring," XP-002082000, SPE 28484, SPE 19th Annual Technical Conference and Exhibition, New Orleans, LA USA, Sep. 25-28, 1994, pp. 215-224.

A. D. Kersey; A Review of Recent Developments in Fiber Optic Sensor Technology, Optical Fiber Technology 2, Article No. 0026, XP-002053711, Feb. 13, 1996, pp. 291-317.

S. Takahashi et al.; "Simultaneous Sensing of Acoustic Wave and Temperature Using a Polarization-Maintaining Fiber," 9th Symposium on Ultrasonic Electronics, Sendai 1988, Japanese Journal of Applied Physics, vol. 28, (1989) Supplement 28-1, pp. 188-10-.

G. Mutter et al.; FOG Based Inertial Strapdown System for Online Borehole Measurements, XP-002082274, Jan. 24, 1994, pp. 681-694.

* cited by examiner

MONITORING OF DOWNHOLE PARAMETERS AND TOOLS UTILIZING FIBER OPTICS

CROSS-REFERENCE TO RELATED APPLICATIONS

This application is a divisional application of U.S. patent application Ser. No. 09/872,591 (now U.S. Pat. No. 6,588,266) filed on Jun. 21, 2001, which is a divisional application of U.S. patent application Ser. No. 09/070,953, (now U.S. Pat. No. 6,268,911), which in turn claimed priority from Provisional U.S. Patent Application Ser. Nos. 60/045,354 filed on May 2, 1997; 60/048,989 filed on Jun. 9, 1997; 60/052,042 filed on Jul. 9, 1997; 60/062,953 filed on Oct. 10, 1997; 67/073,425 filed on Feb. 2, 1998; and 60/079,446 filed on Mar. 26, 1998. Reference is also made to a U.S. Pat. No. 6,281,489 the contents of which are incorporated here by reference.

BACKGROUND OF THE INVENTION

1. Field of the Invention

This invention relates generally to oilfield operations and more particularly to systems and methods utilizing fiber optics for monitoring wellbore parameters, formation parameters, drilling operations, condition of downhole tools installed in the wellbores or used for drilling such wellbores, for monitoring reservoirs and for monitoring of remedial work.

2. Background of the Art

A variety of techniques have been utilized for monitoring reservoir conditions, estimation and quantities of hydrocarbons (oil and gas) in earth formations, for determination formation and wellbore parameters and form determining the operating or physical condition of downhole tools.

Reservoir monitoring typically involves determining certain downhole parameters in producing wellbores, such as temperature and pressure placed at various locations in the producing wellbore, frequently over extended time periods. Wireline tools are most commonly utilized to obtain such measurements, which involves shutting down the production for extended time periods to determine pressure and temperature gradients over time.

Seismic methods wherein a plurality of sensors are placed on the earth=s surface and a source placed at the surface or downhole are utilized to obtain seismic data which is then used to update prior three dimensional (3-D") seismic maps. Three dimensional maps updated over time are sometimes referred to as "4-D" seismic maps. The 4-D maps provide useful information about reservoirs and subsurface structure. These seismic methods are very expensive. The wireline methods are utilized at great time intervals, thereby not providing continuous information about the wellbore conditions or that of the surrounding formations.

Permanent sensors, such as temperature sensors, pressure sensors, accelerometers or hydrophones have been placed in the wellbores to obtain continuous information for monitoring wellbores and the reservoir. Typically, a separate sensor is utilized for each type of parameter to be determined. To obtain such measurements from useful segments of each wellbore, which may contain multilateral wellbores, requires using a large number of sensors, which require a large amount of power, data acquisition equipment and relatively large amount of space, which in many cases is impractical or cost prohibitive.

In production wells, chemicals are often injected downhole to treat the producing fluids. However, it can be difficult to monitor and control such chemical injection in real time. Similarly, chemicals are typically used at the surface to treat the produced hydrocarbons (i.e. break down emulsions) and to inhibit corrosion. However, it can be difficult to monitor and control such treatment in real time.

Formation parameters are most commonly measured by measurement-while-drilling tools during the drilling of the wellbores and by wireline methods after the wellbores have been drilled. The conventional formation evaluation sensors are complex and large in size and thus require large tools. Additionally such sensors are very expensive.

Prior art is also very deficient in providing suitable system and methods for monitoring the condition or health of downhole tools. Tool conditions should be monitored during the drilling process, as the tools are deployed in the wellbore and after deployment, whether during the completion phase or the production phase.

The present invention addresses some of the above-described prior deficiencies and provides systems and methods which utilize a variety of fiber optic sensors for monitoring wellbore parameters, formation parameters, drilling operations, condition of downhole tools installed in the wellbores or used for drilling such wellbores, for monitoring reservoirs and for monitoring of remedial work. In some applications, the same sensor is configured to provide more than one measurement. in many instances these sensors are relatively, consume less power and can operate at higher temperatures than the conventional sensors.

SUMMARY OF THE INVENTION

The present invention provides fiber optics based systems and methods for monitoring downhole parameters and the condition and operation of downhole tools. The sensors may be permanently disposed downhole. The light source for the fiber optic sensors may be disposed in the wellbore or at the surface. The measurements from such sensors may be processed downhole and/or at the surface. Data may also be stored for use for processing. Certain sensors may be configured to provide multiple measurements. The measurements made by the fiber optic sensors in the present invention include temperature, pressure, flow, liquid level, displacement, vibration, rotation, acceleration, acoustic velocity, chemical species, acoustic field, electric field, radiation, pH, humidity, electrical field, magnetic field, corrosion and density.

In one system, a plurality of spaced apart fiber optic sensors are disposed in the wellbore to take the desired measurements. The light source and the processor may be disposed in the wellbore or at the surface. Two way communication between the sensors and the processor is provided via fiber optic links or by conventional methods. A single light source may be utilized in the multilateral wellbore configurations. The sensors may be permanently installed in the wellbores during the completion or production phases. The sensors preferably provide measurements of temperature, pressure and flow for monitoring the wellbore production and for performing reservoir analysis.

In another system the fiber optic sensors are deployed in a production wellbore to monitor the injection operations, fracturing and faults. Such sensors may also be utilized in the injection well. Controllers are provided to control the injection operation in response to the in-situ or real time measurements.

In another system, the fiber optic sensors are used to determine acoustic properties of the formations including acoustic velocity and travel time. These parameters are preferably compensated for the effects of temperature utilizing the downhole temperature sensor measurements. Acoustic measurements are use for cross-well tomography and for updating preexisting seismic data or maps.

The distributed sensors of this invention find particular utility in the monitoring and control of various chemicals which are injected into the well. Such chemicals are injected downhole to address a large number of known problems such as for scale inhibition and for the pretreatment of the fluid being produced. In accordance with the present invention, a chemical injection monitoring and control system includes the placement of one or more sensors downhole in the producing zone for measuring the chemical properties of the produced fluid as well as for measuring other downhole parameters of interest. These sensors are preferably fiber optic based and are formed from a sol gel matrix and provide a high temperature, reliable and relatively inexpensive indicator of the desired chemical parameter. The downhole chemical sensors may be associated with a network of distributed fiber optic sensors positioned along the wellbore for measuring pressure, temperature and/or flow. Surface and/or downhole controllers receive input from the several downhole sensors, and in response thereto, control the injection of chemicals into the brothel.

The chemical parameters are preferably measured in real time and on-line and then used to control the amount and timing of the injection of the chemicals into the wellbore or for controlling a surface chemical treatment system.

An optical spectrometer may be used downhole to determine the properties of downhole fluid. The spectrometer includes a quartz probe in contact with the fluid. Optical energy provided to the probe, preferably from a downhole source. The fluid properties such as the density, amount of oil, water, gas and solid contents affect the refraction of the light. The refracted light is analyzed to determine the fluid properties. The spectrometer may be permanently installed downhole.

The fiber optic sensors are also utilized to measure formation properties, including resistivity, formation acoustic velocity. Other measurements may include electric field, radiation and magnetic field. Such measurements may be made with sensors installed or placed in the wellbore for monitoring the desired formation parameters. Such sensors are also placed in the drill string, particularly in the bottom hole assembly to provide the desired measurements during the drilling of the wellbore.

In another system, the fiber optic sensors are used to monitor the health or physical condition and/or the operation of the downhole tools. The measurements made to monitor the tools include one or more of (a) vibration, (b) noise (c) strain (d) stress (e) displacement (f) flow rate (g) mechanical integrity (h) corrosion (i) erosion (j) scale (k) paraffin and (1) hydrate.

Examples of the more important features of the invention have been summarized rather broadly in order that the detailed description thereof that follows may be better understood, and in order that the contributions to the art maybe appreciated. There are, of course, additional features of the invention that will be described hereinafter and which will form the subject of the claims appended hereto.

BRIEF DESCRIPTION OF THE DRAWINGS

For a detailed understanding of the present invention, reference should be made to the following detailed description of the preferred embodiments, taken in conjunction with the accompanying drawings, in which like elements have been given like numerals, wherein:

FIG. 15 is schematic illustration of a bottomhole assembly for use in drilling wellbores that utilizes with a number of fiber-optic sensors for measuring various downhole parameters during drilling of the wellbores.

DETAILED DESCRIPTION OF PREFERRED EMBODIMENTS

Figure 1:
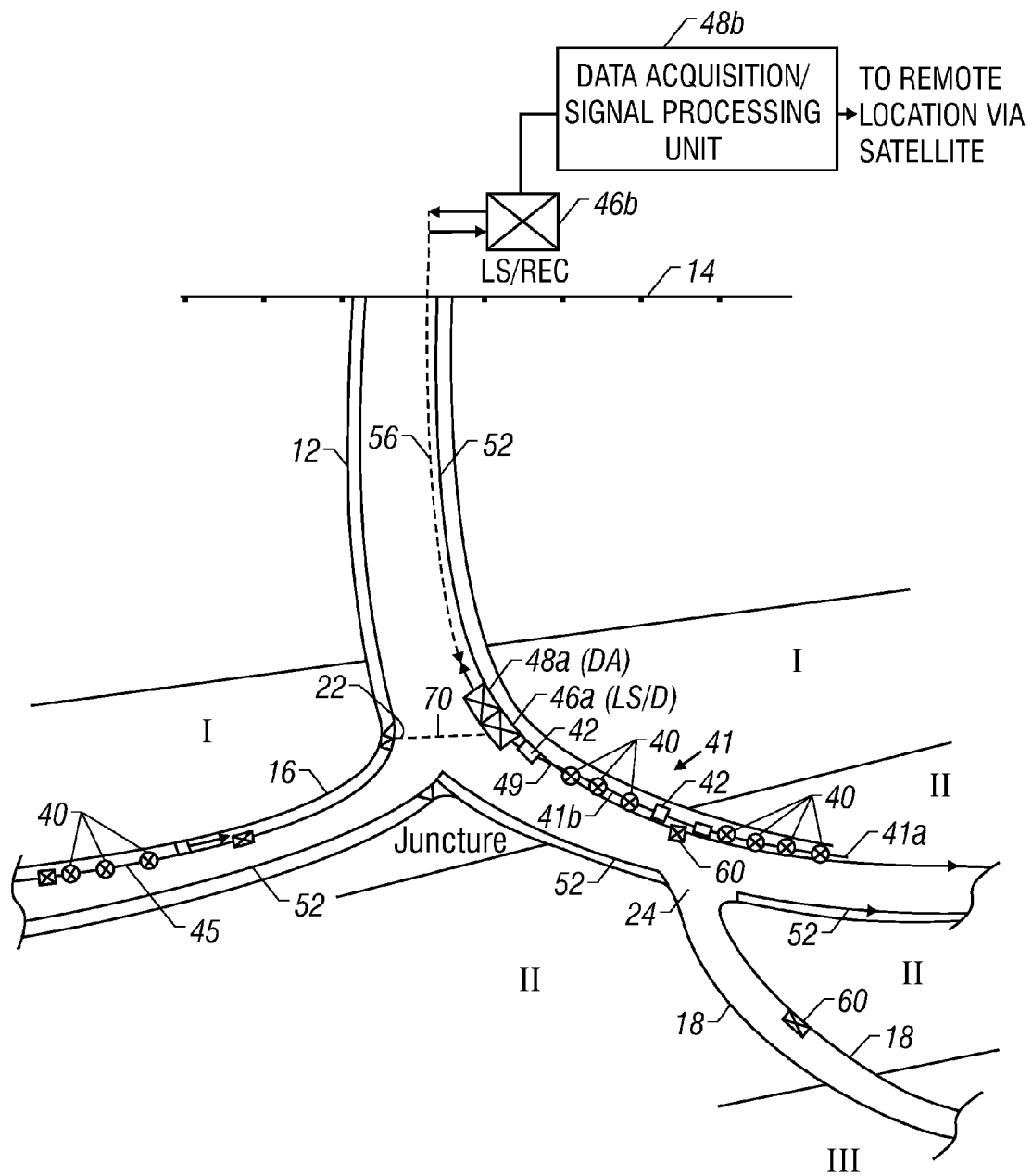
FIG. 1 shows a schematic illustration of a multilateral wellbore system and placement of fiber optic sensors according to one embodiment of the present invention.

FIG. 1 shows an exemplary main or primary wellbore 12 formed from the surface 14 and lateral wellbores 16 and 18 formed from the main wellbore 18. For the purpose of explanation, and not as any limitation, the main wellbore 12 is partly formed in a producing formation or pay zone I and partly in a non-producing formation or dry formation II The lateral wellbore 16 extends from the main wellbore 12 at a juncture 24 into a second producing formation III. For the purposes of illustration, the wellbores herein are shown drilled from land, however, this invention is equally applicable to offshore wellbores. It should be noted that all wellbore configurations shown and described herein are to illustrate the concepts of present invention and shall not be construed to limit the inventions claimed herein.

In one application, a number of fiber optic sensors 40 are place in the wellbore 12. A single or a plurality of fiber optic sensors 40 may be used so as to install the desired number of fiber optic sensors 40 in the wellbore 12. As an example, FIG. 1 shows two serially coupled fiber optic segments 41a and 41b, each containing a plurality of spaced apart fiber optic sensors 40. A light source and detector (LS) 46a coupled to an end 49 of the segment 41a is disposed in the wellbore 12 to transmit light energy to the sensors 40 and to receive the reflected light energy from the sensors 40. A data acquisition and processing unit (TDA) 48a (also referred to herein as a "processor" or "controller") may be disposed downhole to control the operation of the sensors 40, to process downhole sensor signals and data, and to communicate with other equipment and devices, including devices in the wellbores or at the surface (not shown).

Alternatively, a light source 46b and/or the data acquisition and processing unit 48b may be place at the surface 14. Similarly, fiber optic sensor strings 45 may be disposed in other wellbores in the system, such as wellbores 16 and wellbore 18. A single light source, such as the light source 46a or 46b may be utilized for all fiber optic sensors in the various wellbores, such as shown by dotted line 70. Alternatively, multiple light sources and data acquisition units may be used downhole, at the surface or in combination. Since the same sensor may make different types of measurements, the data acquisition unit 48a or 48 is programmed to multiplex the measurement. Also different types of sensors may be multiplexed as required. Multiplexing techniques are know in the art and are thus not described in detail herein. The data acquisition unit 46a may be programmed to control the downhole sensors 40 autonomously or upon receiving command signals from the surface or a combination of these methods.

The sensors 40 may be installed in the wellbores 12, 16, and 18 before or after installing casings in wellbores, such as casing 52 shown installed in the wellbore 12. This may be accomplished by connecting the strings 41a and 41b along the inside of the casing 52. In one method, the strings 41a and 41b may be deployed or installed by robotics devices (not shown). The robotics device would move the sensor strings 41a and 41b within the wellbore 12 to the desired location and install them according to programmed instructions provided to the robotics device. The robotics device may also be utilized to replace a sensor, conduct repairs retrieve the sensors or strings to the surface and monitor the operation of downhole sensors or devices and gather data. Alternatively, the fiber optic sensors 40 maybe placed in the casing 52 (inside, wrapped around, or in the casing wall) at the surface while individual casing sections (which are typically about forty-foot long) are joined prior to conveying the casing sections into the borehole. Stabbing techniques for joining casing or tubing sections are known in the art and are preferred over rotational joints because stabbing generally provides better alignment of the end couplings 42 and also because it allows operators to test and inspect optical connections between segments for proper two-way transmission of light energy through the entire string 41. For coiled tubing applications, the sensors may be wrapped on the outside or placed in conduit inside the tubing. Light sources and data acquisition unit may also be placed in the coiled tubing prior to or after deployment.

Thus, in the system described in FIG. 1, a plurality of fiber optic sensors 40 are installed spaced apart in one or more wellbores, such as wellbores 12, 16 and 18. If desired, each fiber optic sensor 40 can be configured to operate in more than one mode to provide a number of different measurements. The light source 46a, and data detection and acquisition system 48a may be placed downhole or at the surface. Although each fiber optic sensor 40 may provide measurements for multiple parameters, such sensors are still relatively small compared to individual commonly used single measurement sensors, such as pressure sensors, stain gauges, temperature sensors, flow measurement devices and acoustic sensors. This enables making a large number of different types of measurements utilizing relatively small downhole space. Installing data acquisition and processing devices or units 48a downhole allows making a large number of data computations and processing downhole, avoiding the need of transmitting large amounts of data to the surface. Installing the light source 46a downhole allows locating the source 46a close to the sensors 40, which avoids transmitting light to great distances from the surface thus avoiding loss of light energy. The data from the downhole acquisition system 48a may be transmitted to the surface by any suitable communication links or method including optical fibers, wire connections, electromagnetic telemetry and acoustic methods. Data and signals may be transmitted downhole using the same communication links. Still in some applications, it may be desirable to locate the light source 46b and/or the data acquisition and processing system 48b at the surface. Also, in some cases, it may be more advantageous to partially process data downhole and partially at the surface.

In the present invention, the fiber optic sensors 40 may be configured to provide measurements for temperature, pressure, flow, liquid level displacement, vibration, rotation, acceleration, velocity, chemical species, radiation, pH, humidity, electric fields, acoustic fields and magnetic fields.

Still referring to FIG. 1, any number of conventional sensors, generally denoted herein by numeral 60, may be disposed in any of the wellbores 12, 16 and 18. Such sensors may include sensors for determining resistivity of fluids and formations, gamma rays sensors and hydrophones. The measurements from the fiber optic sensors 40 and sensors 60 may be combined to determine the various conditions downhole. For example flow measurements from fiber optic sensors and the resistivity measurements from conventional sensors may be combined to determine water saturation or to determine the oil, gas an water content. Alternatively, the fiber optic sensors may be utilized to determine the same parameters.

In one mode, the fiber optic sensors are permanently installed in the wellbores at selected locations. In a producing wellbore, the sensors continuously or periodically (as programmed) provide the pressure and/or temperature and/or fluid flow measurements. Such measurements are preferably made for each producing zone in each of the wellbores. To perform certain types of reservoir analysis, it is required to know the temperature and pressure build rates in the wellbores. This requires measuring the temperature and pressure at selected locations downhole over extended time period after shutting down the well at the surface. In the prior art methods, the well is shut down at the surface, a wireline tool is conveyed in to the wellbore and positioned at one location in the wellbore. The tool continuously measure temperature and pressure and may provide other measurements, such as flow control. These measurements are then utilized to perform reservoir analysis, which may include determining the extent of the hydrocarbon reserves remaining in a field, flow characteristics of the fluid from the producing formations, water content, etc.

The above-described prior art methods do not provide continuous measurements while the well is producing and requires special wireline tools that must be conveyed downhole. The present invention, on the other hand, provides in-situ measurements while the wellbore is producing. The fluid flow information from each zone is used to determine the effectiveness of each producing zone. Decreasing flow rates over time may indicate problems with the flow control devices, such as screens and sliding sleeves, or clogging of the perforations and rock matrix near the wellbore. This information is used to determine the course of action, which may include further opening or closing sliding sleeves to increase or decrease the production rate, remedial work, such as cleaning or reaming operations, shutting down a particular zone, etc. The temperature and pressure measurements are used to continually monitor each production zone and to update reservoir models. To make measurement for determining the temperature and pressure buildup rates, the wellbores are shut down and making of measurements continues. This does not require transporting wireline tools to the location, which can be very expensive for offshore wellbores and wellbores drilled in remote locations. Further, the in-situ measurements and computed data can be communicated to a central office or to the offices of log and reservoir engineers via satellite. This continuous monitoring of wellbores allows taking relatively quick action, which can significantly improve the hydrocarbon production from the wellbores. The above described measurements may also be taken for non-producing zones, such as zone II, to aid in reservoir modeling, to determine the effect of production from various wellbores on the field in which the wellbores are drilled. Optical spectrometers, as described later may be used to determine the constituents of the formation fluid and certain chemical properties of such fluids. Presence of gas may be detected to prevent blow-outs or to take other actions.

Figure 2:
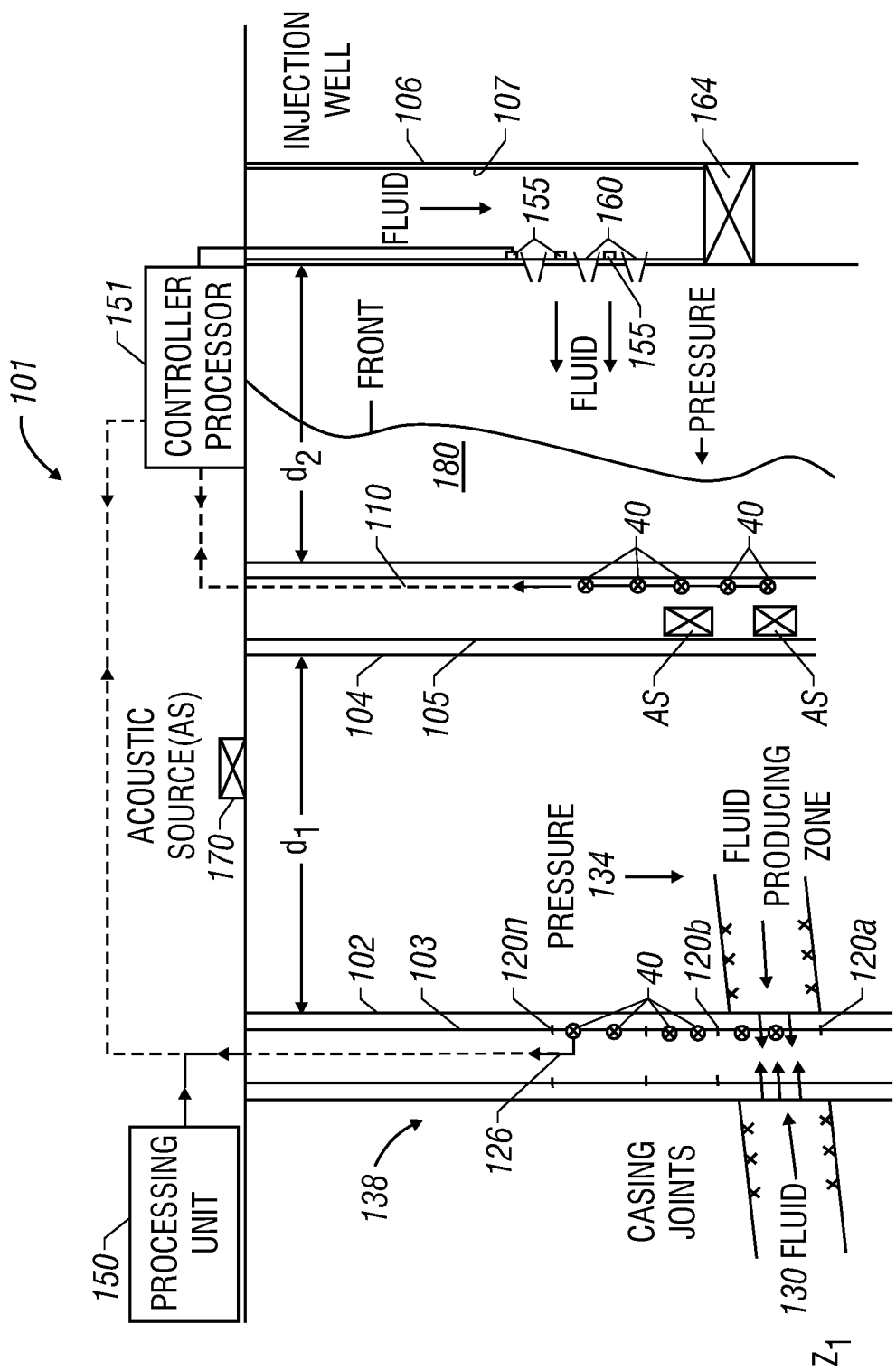
FIG. 2 shows a schematic illustration of a configurations of wellbores using fiber-optic sensor arrangements according to the present invention to: (a) to detect and monitor compressive stresses exerted on wellbore casings and formations; (b) determine the effectiveness of the injection process and in-situ control of the injection operations, and (c) make acoustic measurements for cross-well tomography and to generate and/or update subsurface seismic maps.

FIG. 2 shows a plurality of wellbores 102, 104 and 106 formed in a field 101 from the earth=s surface 110. The wellbores in FIG. 2 are configured to describe the use of the fiber-optic sensor arrangements according to the present invention to: (a) detect compressive stresses exerted into wellbore casings due to depletion of hydrocarbons or other geological phenomena; (b) determine the effectiveness of injection operations and for in-situ monitoring and control of such operations, and (c) make acoustic measurements for cross-well tomography and to generate and/or update subsurface seismic maps.

As an example only, and not as any limitation, FIG. 2 shows three wellbores 102, 104 and 106 formed in a common field or region of interest 101. For the purpose of illustration, the wellbores 102, 104 and 106 are shown lined with respective casings 103, 105 and 107. Wellbore 102 contains a string 122 of fiber-optic sensors 40. The signals and data between the downhole sensor strings 122 and the surface 110 are communicated via a two-way telemetry link 126. The casing 103 may be made by coupling or joining tubulars or casing sections at the surface prior to their insertion into the wellbore 102. The casing joints are shown by numerals 120a-n, which as indicated are typically about forty (40) feet apart. Coiled tubing may also be used as the casing.

The wellbore 102 has a production zone 130 from which hydrocarbons are produced via perforations 132 made in the casing 103. The production zone 130 depletes as the fluid flows from the production zone 130 into the wellbore 102. If the production rate is high, the rate of fluid depletion in the formations surrounding the production zone 130 may be greater than the rate at which fluids can migrate into the formation to fill the depleted pores. The weight of the formation 138 above the production zone exerts pressure 134 on the zone 130. If the pressure 134 is grater than what the rock matrix of the zone 130 can support, it starts to collapse, thereby exerting compressive stress on the casing 103. If the compressive stress is excessive, the casing 103 may break at one or more of the casing joints 102a-n. In case of the coiled tubing, it may buckle or collapse due to stresses. The stresses can also occur due to natural geological changes, such as shifting of the subsurface strata or due to deletion by other wells in the field 101.

To detect compressive stresses in the casing 103, the fiber optic sensors 40 may be operated in the mode that provides strain gauge type of measurements, which are then utilized to determine the extent of the compressive stress on the casing 103. Since the sensor string 122 spans several joints, the system can be used to determine the location of the greatest stress in the casing 103 and the stress distribution along any desired section of the casing 103. This information may be obtained periodically or continuously during the life of the wellbore 102. Such monitoring of stresses provides early warning about the casing health or physical condition and the condition of the zone 130. This information allows the operator of the wellbore 102 to either decrease the production from the wellbore 102 or to shut down the well bore 102 and take remedial measures to correct the problem.

The use of the fiber optic sensors to determine the effectiveness of remedial operations, such as fracturing or injection, will be described while referring to wellbores 104 and 106 of FIG. 2. Wellbore 104 is shown located at a distance "$d_1$" from the wellbore 102 and the wellbore 106 at a distance "$d_2$" from the wellbore 104. A string 124 containing a number of spaced apart fiber-optic sensors 40 is disposed in the wellbore 104. The length of the string 124 and the number of sensors 40 and their spacing depends upon the specific application. The signals and data between the string 124 and a surface equipment 151 are communicated over a two-way telemetry or communications link 128.

For the purpose of illustration and not as any limitation, the wellbore 106 will be utilized for injection purposes. The wellbore 106 contains perforated zone 160. The wellbore is plugged by a packer or any other suitable device 164 below the perforations to prevent fluid flow beyond or downhole of the packer 164. To perform an injection operation, such as for fracturing the formation around the wellbore 106 or to stimulate the production from other wellbores in the field 101, such as the wellbore 104, a suitable fluid 166 (such as steam) migrates toward the wellbore 104 and may create a fluid wall 107a. This causes the pressure across the wellbore 104 and fluid flow from the formation 180 into the wellbore 104 may increase. Fracturing of the formation 180 into the wellbore 104 may increase. Additionally, the fracturing of the formation 180 generates seismic waves, which generate acoustic energy. The fiber optic sensors 40 along with any other desired sensors disposed in the wellbore 104 measure the changes in the pressure, temperature, fluid flow, acoustic signals along the wellbore 104. The sensor measurements (signals) are processed to determine the effectiveness of the injection operations. For example, the change in pressure, fluid flow at the wellbore 104 and the time and amount of injected material can be used to determine the effectiveness of the injection operations. Also, acoustic signals received at the wellbore provide useful information about the extent of fracturing of the rock matrix of formation 180. Also, the acoustic signals received at the wellbore provide useful information about the extent of fracturing of the rock matrix for the formation 100. The acoustic signal analysis is used to determine whether to increase or decrease the pressure of the injected fluids 166 or to terminate the operation. This method enables the operators to continuously monitor the effect of the injection operation in one wellbore, such as the wellbore 106, upon the other wellbores in the field, such as wellbore 104.

The sensor configuration shown in FIG. 2 may be utilized to map subsurface formations. In one method, an acoustic source (AS) 170, such as a vibrator or an explosive charge, is activated at the surface 110. The sensors 40 in the wellbores 102 and 104 detect acoustic signals which travel from the source 170 to the sensors 40 through the formation 180. These signals are processed by any of the methods known in the art to map the subsurface formations and/or update the existing maps, which are typically obtained prior to drilling wellbores, such as wellbores 102 and 104. Two dimensional or three dimensional seismic maps are commonly obtained before drilling wellbores. The data obtained by the above-described method is used to update such maps. Updating three dimensional or 3D maps over time provides what are referred to in the oil and gas industry as four dimensional or "4D" maps. These maps are then used to determine the conditions of the reservoirs, to perform reservoir modeling and to update existing reservoir models. These reservoir models are used to manage the oil and gas production from the various wellbores in the field. The acoustic data obtained above is also utilized for cross-well tomography. Also, the acoustic source 170 may be disposed (activated) within one or more of the wellbores, such as shown by numeral 170 in wellbore 104. The acoustic source is moved to other locations, such as shown by dotted box 170 to take additional measurements. The fiber optic sensors described herein may be permanently deployed in the wellbores.

Figure 3:
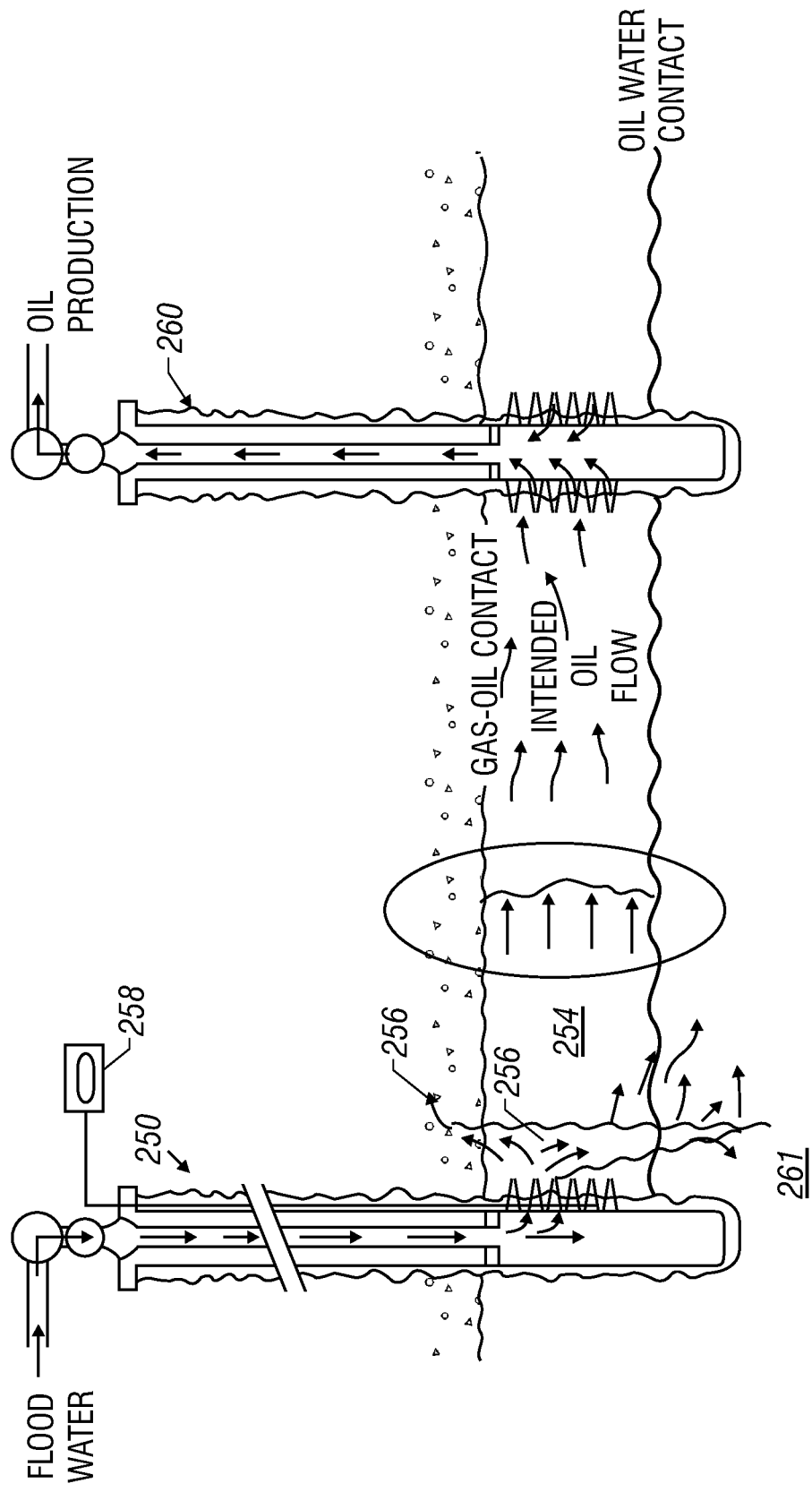
FIG. 3 is a schematic illustrating both an injection well and a production well having sensors and flood front running between the wells and loss through unintended fracturing.

In another embodiment of the invention relating to fracturing, illustrated schematically in FIG. 3, downhole sensors measure strain induced in the formation by the injected fluid. Strain is an important parameter for avoiding exceeding the formation parting pressure or fracture pressure of the formation with the injected fluid. By avoiding the opening of or widening of natural pre-existing fractures large unswept areas of the reservoir can be avoided. The reason this information is important in the regulation of pressure of the fluid to avoid such activity is that when pressure opens fractures or new fractures are created there is a path of much less resistance for the fluid to run through. Since the injection fluid will follow along the path of least resistance it would generally run in the fractures and around areas of the reservoir that need to be swept. This substantially reduces its efficiency. The situation is generally referred to in the art as an artificially high permeability channel. Another detriment to such a condition is the uncontrolled loss of injected fluids. This results in loss of oil due to the reduced efficiency of the sweep and additionally may function as an economic drain due to the loss of expensive fluids.

FIG. 3 schematically illustrates the embodiment and the condition set forth above by illustrating an injection well 250 and a production well 260. Fluid 252 is illustrated escaping via the unintended fracture from the formation 254 into the overlying gas cap level 256 and the underlying water table 261. The condition is avoided by the invention by using pressure sensors to limit the injection fluid pressure as described above. The rest of the fluid 252 is progressing as it is intended to through the formation 254. In order to easily and reliably determine what the stress is in the formation 54, fiber optic acoustic sensors 256 are located in the injection well 250 at various points therein. The acoustic sensors 256 pick up sounds generated by stress in the formation which propagate through the reservoir fluids or reservoir matrix to the injection well. In general, higher sound levels would indicate severe stress in the formation and should generate a reduction in pressure of the injected fluid whether by automatic control or by technician control. A data acquisition system 258 is preferable to render the system extremely reliable and system 258 may be at the surface where it is illustrated in the schematic drawing or may be downhole. Based upon acoustic signals received the system of the invention, preferably automatically, although manually is workable, reduces pressure of the injected fluid by reducing pump pressure. Maximum sweep efficiency is thus obtained.

Figure 4:
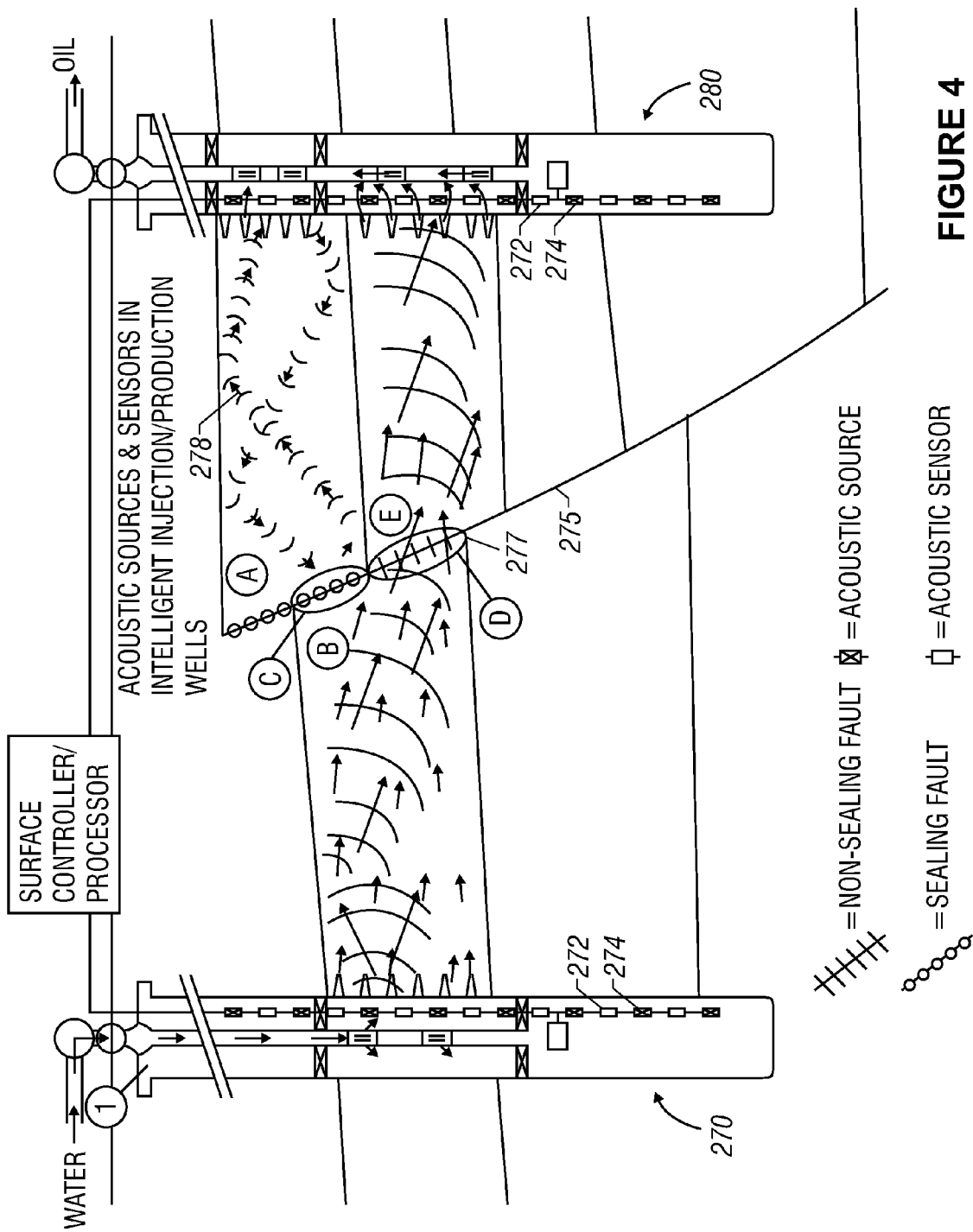
FIG. 4 is a schematic representation wherein the production wells are located on either side of the injection well.

In yet another embodiment of the invention, as schematically illustrated in FIG. 4, acoustic generators and receivers are employed to determine whether a formation which is bifurcated by a fault is sealed along the fault or is permeable along the fault. It is known by one of ordinary skill in the art that different strata within a formation bifurcated by a fault may have some zones that flow and some zones that are sealed; this is the illustration of FIG. 4. Referring directly to FIG. 4, injection well 270 employs a plurality of fiber optic sensors 272 and acoustic generators 274 which, most preferably, alternate with increasing depth in the wellbore. In production well 280, a similar arrangement of sensors 272 and acoustic generators 274 are positioned. The sensors and generators are preferably connected to processors which are either downhole or on the surface and preferably also connect to the associated production or injection well. The sensors 272 can receive acoustic signals that are naturally generated in the formation, generated by virtue of the fluid flowing through the formation from the injection well and to the production well and also can receive signals which are generated by signal generators 274. Where signal generators 274 generate signals, the reflected signals that are received by sensors 272 over a period of time can indicate the distance and acoustic volume through which the acoustic signals have traveled. This is illustrated in area A of FIG. 4 in that the fault line 275 is sealed between area A and area B on the figure. This is illustrated for purposes of clarity only by providing circles 276 along fault line 275. The areas of fault line 275 which are permeable are indicated by hash marks 277 through fault line 275. Since the acoustic signal represented by arrows and semi-curves and indicated by numeral 278 cannot propagate through the area C which bifurcates area A from area B on the left side of the drawing, that signal will bounce and it then can be picked up by sensor 272. The time delay, number and intensity of reflections and mathematical interpretation which is common in the art provides an indication of the lack of pressure transmissivity between those two zones. Additionally this pressure transmissivity can be confirmed by the detection by said acoustic signals by sensors 272 in the production well 280. In the drawing, the area directly beneath area A, indicated as area E, is permeable to area B through fault 275 because the region D in that area is permeable and will allow flow of the flood front from the injection well 270 through fault line 275 to the production well 280. Acoustic sensors and generators can be employed here as well since the acoustic signal will travel through the area D and, therefore, reflection intensity to the receivers 272 will decrease. Time delay will increase. Since the sensors and generators are connected to a central processing unit and to one another it is a simple operation to determine that the signal, in fact, traveled from one well to the other and indicates permeability throughout a particular zone. By processing the information that the acoustic generators and sensors can provide the injection and production wells can run automatically by determining where fluids can flow and thus opening and closing valves at relevant locations on the injection well and production well in order to flush production fluid in a direction advantageous to run through a zone of permeability along the fault.

Other information can also be generated by this alternate system of the invention since the sensors 272 are clearly capable of receiving not only the generated acoustic signals but naturally occurring acoustic waveforms arising from both the flow of the injected fluids as the injection well and from those arising within the reservoirs in result of both fluid injection operations and simultaneous drainage of the reservoir in resulting production operations. The preferred permanent deployment status of the sensors and generators of the invention permit and see to the measurements simultaneously with ongoing injection flooding and production operations. Advancements in both acoustic measurement capabilities and signal processing while operating the flooding of the reservoir represents a significant, technological advance in that the prior art requires cessation of the injection/production operations in order to monitor acoustic parameters downhole. As one of ordinary skill in the art will recognize the cessation of injection results in natural redistribution of the active flood profile due primarily to gravity segregation of fluids and entropic phenomena that are not present during active flooding operations. This also enhances the possibility of premature breakthrough, as oil migrates to the relative top of the formation and the injected fluid, usually water, migrates to the relative bottom of the formation. Hence, there is a significant possibility that the water will actually reach the production well and thus further pumping of steam or water will merely run underneath the layer of oil at the top of the formation and the sweep of that region would be extremely difficult thereafter.

In yet another embodiment of the invention fiber optics are employed (similar to those disclosed in the U.S. Provisional Patent application Ser. No. 60/048,989 filed on Jun. 10, 1997, which is fully incorporated herein by reference) to determine the amount of and/or presence of biofouling within the reservoir by providing a culture chamber within the injection or production well, wherein light of a predetermined wavelength may be injected by a fiber optical cable, irradiating a sample determining the degree to which biofouling may have occurred. As one of ordinary skill in the art will recognize, various biofouling organisms will have the ability to fluoresce at a given wavelength, that wavelength once determined, is useful for the purpose above stated.

Referring back to FIG. 2, the flood front may also be monitored from the "back" employing sensors 155 installed in the injection well 106. These sensors provide acoustic signals which reflect from the water/oil interface thus providing an accurate picture in a moment in time of the three-dimensional flood front. Taking real time 4D pictures provides an accurate format of the density profile of the formation due to the advancing flood front. Thus, a particular profile and the relative advancement of the front can be accurately determined by the density profile changes. It is certainly possible to limit the sensors and acoustic generators to the injection well for such a system. However, it is generally more preferable to also introduce sensors and acoustic generators in the production well toward which the front is moving (as described before) thus allowing an immediate double check of the fluid front profile. That is, acoustic generators on the production well will reflect a signal off the oil/water interface and will provide an equally accurate three-dimensional fluid front indicator. The indicators from both sides of the front should agree and thus provides an extremely reliable indication of location and profile. A common processor 151 may be used for processing data from the wells 102-106.

Figure 5:
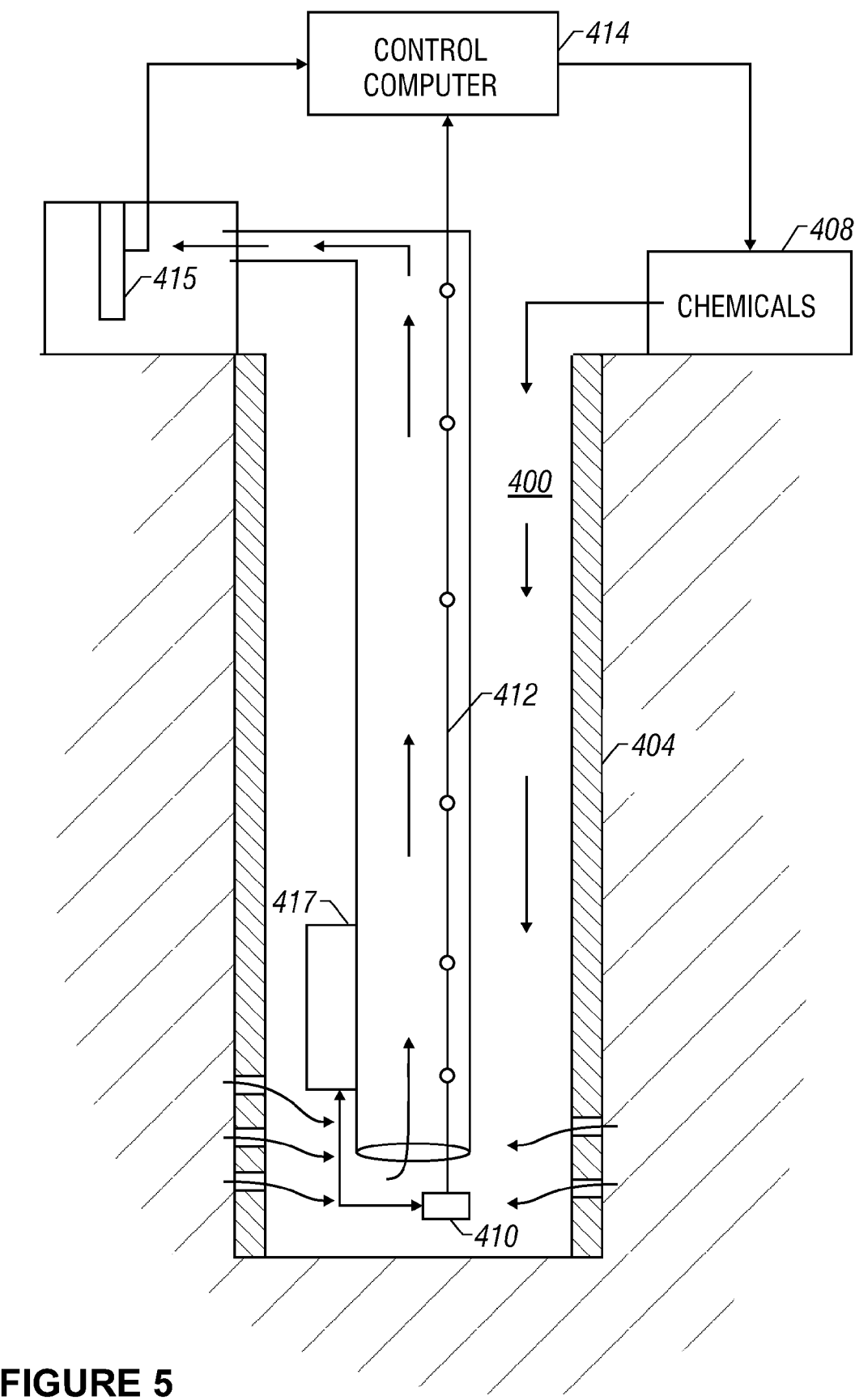
FIG. 5 is a schematic illustration of a chemical injection monitoring and control system utilizing a distributed sensor arrangement and downhole chemical monitoring sensor system in accordance with one embodiment of the present invention.

Referring now to FIG. 5, the distributed fiber optic sensors of the type described above are also well suited for use in a production well where chemicals are being injected therein and there is a resultant need for the monitoring of such a chemical injection process so as to optimize the use and effect of the injected chemicals. Chemicals often need to be pumped down a production well for inhibiting scale, paraffins and the like as well as for other known processing applications and pretreatment of the fluids being produced. Often, as shown in FIG. 5, chemicals are introduced in an annulus 400 between the production tubing 402 and the casing 404 of a well 406. The chemical injection (shown schematically at 408) can be accomplished in a variety of known methods such as in connection with a submersible pump (as shown for example in U.S. Pat. No. 4,582,131, assigned to the assignee hereof and incorporated herein by reference) or through an auxiliary line associated with a cable used with an electrical submersible pump (such as shown for example in U.S. Pat. No. 5,528,824, assigned to the assignee hereof and incorporated herein by reference).

In accordance with an embodiment of the present invention, one or more bottomhole sensors 410 are located in the producing zone 405 for sensing a variety of parameters associated with the producing fluid and/or interaction of the injected chemical and the producing fluid 407. Thus, the bottomhole sensors 410 will sense parameters relative to the chemical properties of the produced fluid such as the potential ionic content, the covalent content, pH level, oxygen levels, organic precipitates and like measurements. Sensors 410 can also measure physical properties associated with the producing fluid and/or the interaction of the injected chemicals and producing fluid such as the oil/water cut, viscosity and percent solids. Sensors 410 can also provide information related to paraffin and scale build-up, $H_2S$ content and the like.

Bottomhole sensors 410 preferably communicate with and/or are associated with a plurality of distributed sensors 412 which are positioned along at least a portion of the wellbore (e.g., preferably the interior of the production tubing) for measuring pressure, temperature and/or flow rate as discussed above in connection with FIG. 1. The present invention is also preferably associated with a surface control and monitoring system 414 and one or more known surface sensors 415 for sensing parameters related to the produced fluid; and more particularly for sensing and monitoring the effectiveness of treatment rendered by the injected chemicals. The sensors 415 associated with surface system 414 can sense parameters related to the content and amount of, for example, hydrogen sulfide, hydrates, paraffins, water, solids and gas.

Preferably, the production well disclosed in FIG. 5 has associated therewith a so-called Aintelligent@ downhole control and monitoring system which may include a downhole computerized controller 418 and/or the aforementioned surface control and monitoring system 414. This control and monitoring system is of the type disclosed in U.S. Pat. No. 5,597,042, which is assigned to the assignee hereof and fully incorporated herein by reference. As disclosed in U.S. Pat. No. 5,597,042, the sensors in the "intelligent" production wells of this type are associated with downhole computer and/or surface controllers which receive information from the sensors and based on this information, initiate some type of control for enhancing or optimizing the efficiency of production of the well or in some other way effecting the production of fluids from the formation. In the present invention, the surface and/or downhole computers 414, 418 will monitor the effectiveness of the treatment of the injected chemicals and based on the sensed information, the control computer will initiate some change in the manner, amount or type of chemical being injected. In the system of the present invention, the sensors 410 and 412 may be connected remotely or in-situ.

In a preferred embodiment of the present invention, the bottomhole sensors comprise fiber optic chemical sensors. Such fiber optic chemical sensors preferably utilize fiber optic probes which are used as a sample interface to allow light from the fiber optic to interact with the liquid or gas stream and return to a spectrometer for measurement. The probes are typically composed of sol gel indicators. Sol gel indicators allow for on-line, real time measurement and control through the use of indicator materials trapped in a porous, sol gel derived, glass matrix. Thin films of this material are coated onto optical components of various probe designs to create sensors for process and environmental measurements. These probes provide increased sensitivity to chemical species based upon characteristics of the specific indicator. For example, sol gel probes can measure with great accuracy the pH of a material and sol gel probes can also measure for specific chemical content. The sol gel matrix is porous, and the size of the pores is determined by how the glass is prepared. The sol gel process can be controlled so as to create a sol gel indicator composite with pores small enough to trap an indicator in the matrix but large enough to allow ions of a particular chemical of interest to pass freely in and out and react with the indicator. An example of suitable sol gel indicator for use in the present invention is shown in FIGS. 6 and 7.

Figure 6:
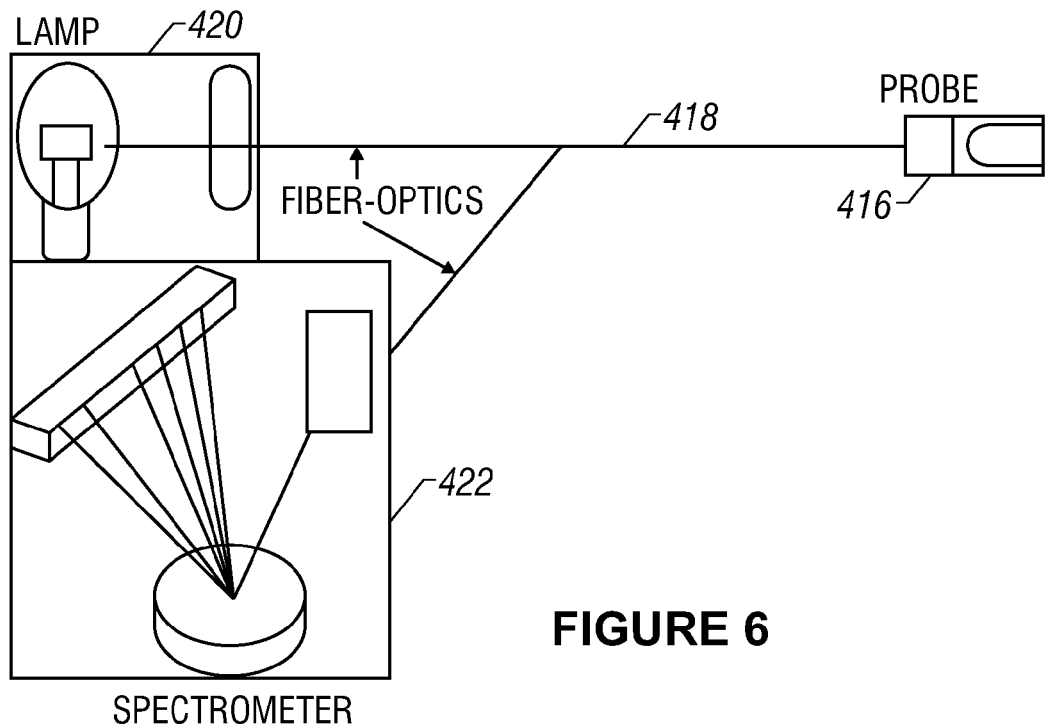
FIG. 6 is a schematic illustration of a fiber optic sensor system for monitoring chemical properties of produced fluids.
Figure 7:
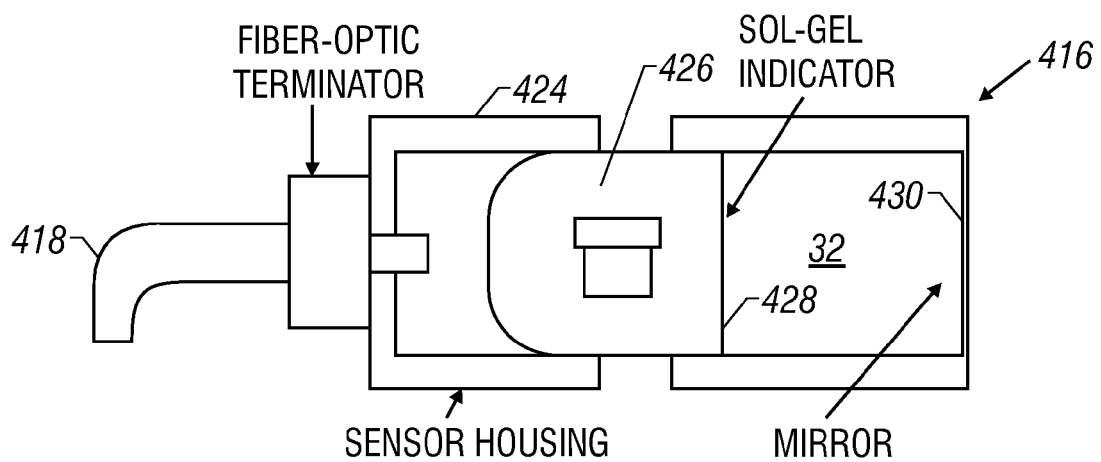
FIG. 7 is a schematic illustration of a fiber optic sol gel indicator probe for use with the sensor system of FIG. 6.

Referring to FIGS. 6 and 7, a probe is shown at 416 connected to a fiber optic cable 418 which is in turn connected both to a light source 420 and a spectrometer 422. As shown in FIG. 7, probe 416 includes a sensor housing 424 connected to a lens 426. Lens 426 has a sol gel coating 428 thereon which is tailored to measure a specific downhole parameter such as pH or is selected to detect the presence, absence or amount of a particular chemical such as oxygen, $H_2S$ or the like. Attached to and spaced from lens 426 is a mirror 430. During use, light from the fiber optic cable 418 is collimated by lens 426 whereupon the light passes through the sol gel coating 428 and sample space 432. The light is then reflected by mirror 430 and returned to the fiber optical cable. Light transmitted by the fiber optic cable is measured by the spectrometer 422. Spectrometer 422 (as well as light source 420) may be located either at the surface or at some location downhole. Based on the spectrometer measurements, a control computer 414, 416 will analyze the measurement and based on this analysis, the chemical injection apparatus 408 will change the amount (dosage and concentration), rate or type of chemical being injected downhole into the well. Information from the chemical injection apparatus relating to amount of chemical left in storage, chemical quality level and the like will also be sent to the control computers. The control computer may also base its control decision on input received from surface sensor 415 relating to the effectiveness of the chemical treatment on the produced fluid, the presence and concentration of any impurities or undesired by-products and the like.

Alternatively a spectrometer may be utilized to monitor certain properties of downhole fluids. The sensor includes a glass or quartz probe, one end or tip of which is placed in contact with the fluid. Light supplied to the probe is refracted based on the properties of the fluid. Spectrum analysis of the refracted light is used to determine the and monitor the properties, which include the water, gas, oil and solid contents and the density.

In addition to the bottomhole sensors 410 being comprised of the fiber optic sol gel type sensors, distributed sensors 412 along production tubing 402 may also include the fiber optic chemical sensors of the type discussed above. In this way, the chemical content of the production fluid may be monitored as it travels up the production tubing if that is desirable.

The permanent placement of the sensors 410, 412 and control system 417 downhole in the well leads to a significant advance in the field and allows for real time, remote control of chemical injections into a well without the need for wireline device or other well interventions.

Figure 8:
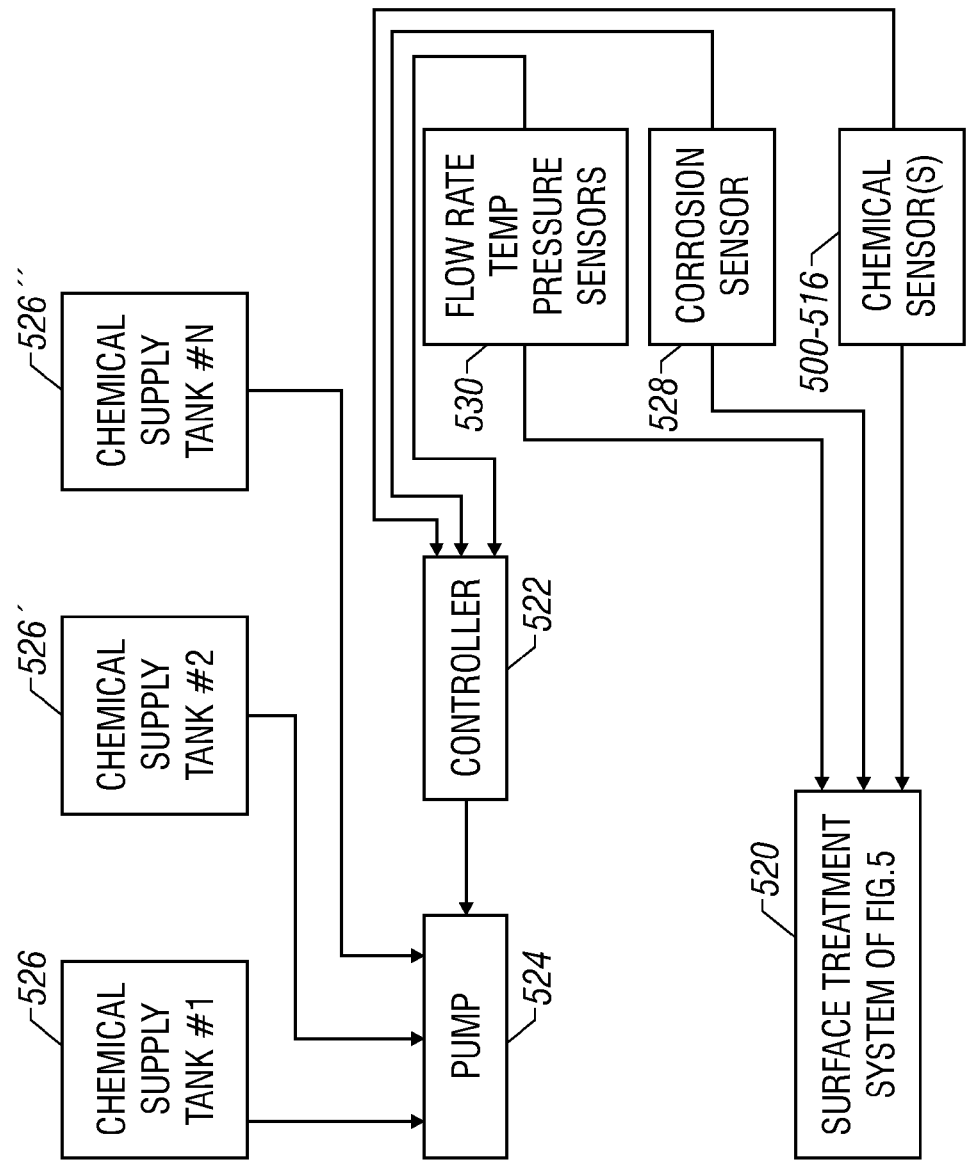
FIG. 8 is a schematic illustration of a surface treatment system in accordance with the present invention.

In accordance with the present invention, a novel control and monitoring system is provided for use in connection with a treating system for handling produced hydrocarbons in an oilfield. Referring to FIG. 8, a typical surface treatment system used for treating produced fluid in oil fields is shown. As is well known, the fluid produced from the well includes a combination of emulsion, oil, gas and water. After these well fluids are produced to the surface, they are contained in a pipeline known as a "flow line". The flow line can range in length from a few feet to several thousand feet. Typically, the flow line is connected directly into a series of tanks and treatment devices which are intended to provide separation of the water in emulsion from the oil and gas. In addition, it is intended that the oil and gas be separated for transport to the refinery.

The produced fluids flowing in the flow line and the various separation techniques which act on these produced fluids lead to serious corrosion problems. Presently, measurement of the rate of corrosion on the various metal components of the treatment systems such as the piping and tanks is accomplished by a number of sensor techniques including weight loss coupons, electrical resistance probes, electrochemical—linear polarization techniques, electrochemical noise techniques and AC impedance techniques. While these sensors are useful in measuring the corrosion rate of a metal vessel or pipework, these sensors do not provide any information relative to the chemicals themselves, that is the concentration, characterization or other parameters of chemicals introduced into the treatment system. These chemicals are introduced for a variety of reasons including corrosion inhibition and emulsion breakdown, as well as scale, wax, asphaltene, bacteria and hydrate control.

In accordance with an important feature of the present invention, sensors are used in chemical treatment systems of the type disclosed in FIG. 8 which monitors the chemicals themselves as opposed to the effects of the chemicals (for example, the rate of corrosion). Such sensors provide the operator of the treatment system with a real time understanding of the amount of chemical being introduced, the transport of that chemical throughout the system, the concentration of the chemical in the system and like parameters. Examples of suitable sensors which may be used to detect parameters relating to the chemicals in the treatment system include the fiber optic sensor described above with reference to FIGS. 6 and 7. Ultrasonic absorption and reflection, laser-heated cavity spectroscopy (LIMS), X-ray fluorescence spectroscopy, neutron activation spectroscopy, pressure measurement, microwave or millimeter wave radar reflectance or absorption, and other optical and acoustic (i.e., ultrasonic or sonar) methods may also be used. A suitable microwave sensor for sensing moisture and other constituents in the solid and liquid phase influent and effluent streams is described in U.S. Pat. No. 5,455,516, all of the contents of which are incorporated herein by reference. An example of a suitable apparatus for sensing using LIBS is disclosed in U.S. Pat. No. 5,379,103 all of the contents of which are incorporated herein by reference.

An example of a suitable apparatus for sensing LIMS is the LASMA Laser Mass Analyzer available from Advanced Power Technologies, Inc. of Washington, D.C. An example of a suitable ultrasonic sensor is disclosed in U.S. Pat. No. 5,148,700 (all of the contents of which are incorporated herein by reference). A suitable commercially available acoustic sensor is sold by Entech Design, Inc., of Denton, Tex. under the trademark MAPS[7]. Preferably, the sensor is operated at a multiplicity of frequencies and signal strengths. Suitable millimeter wave radar techniques used in conjunction with the present invention are described in chapter 15 of Principles and Applications of Millimeter Wave Radar, edited by N. C. Currie and C. E. Brown, Artech House, Norwood, Mass. 1987.

While the sensors may be utilized in a system such as shown in FIG. 8 at a variety of locations, the arrows numbered 500, through 516 indicate those positions where information relative to the chemical introduction would be especially useful.

Figure 9:
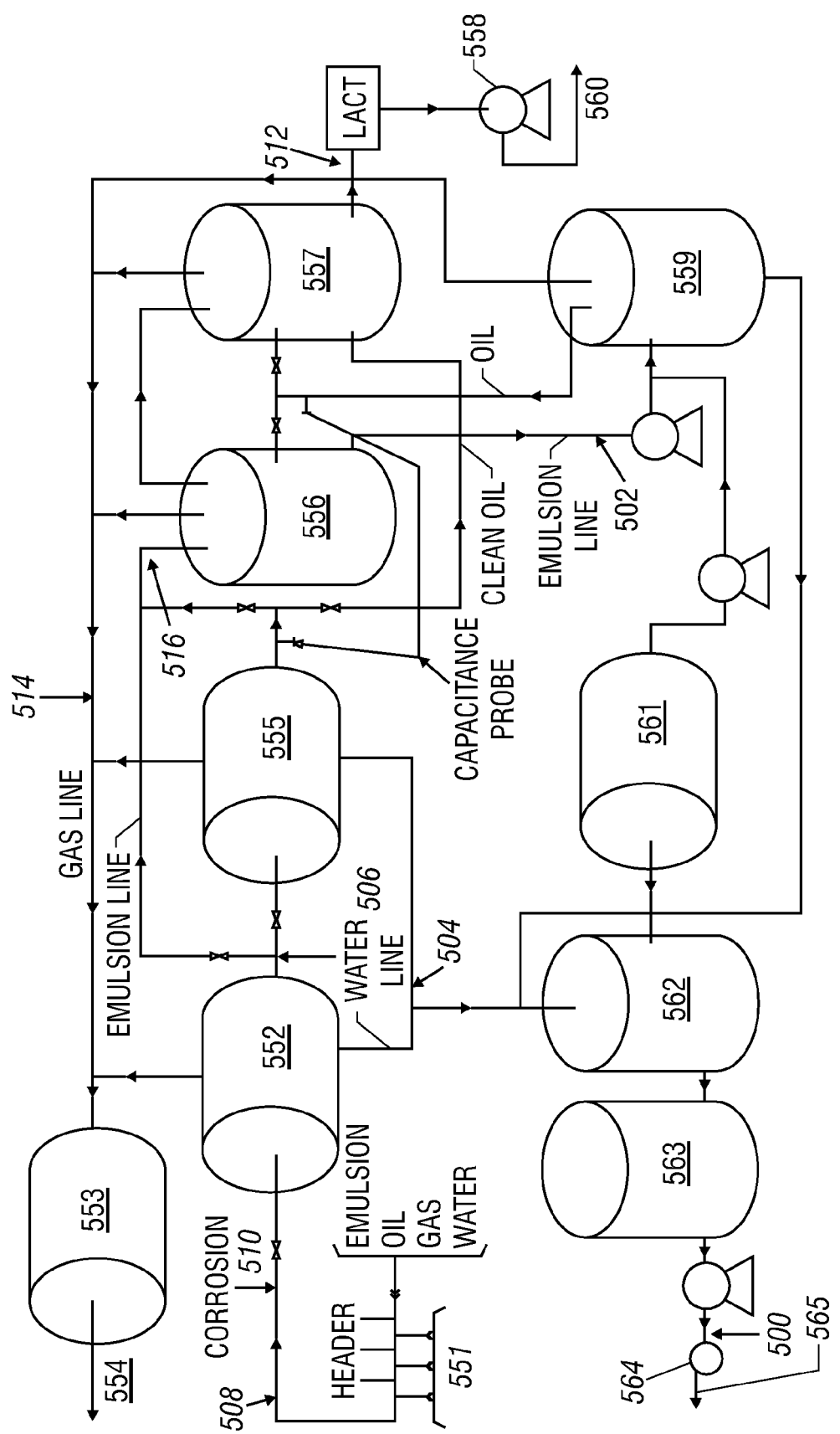
FIG. 9 is a schematic of a control and monitoring system for the surface treatment system of FIG. 8.

Referring now to FIG. 9, the surface treatment system of FIG. 8 is shown generally at 520. In accordance with the present invention, the chemical sensors (i.e. 500-516) will sense, in real time, parameters (i.e., concentration and classification) related to the introduced chemicals and supply that sensed information to a controller 522 (preferably a computer or microprocessor based controller). Based on that sensed information monitored by controller 522, the controller will instruct a pump or other metering device 524 to maintain, vary or otherwise alter the amount of chemical and/or type of chemical being added to the surface treatment system 520. The supplied chemical from tanks 526 can, of course, comprise any suitable treatment chemical such as those chemicals used to treat corrosion, break down emulsions, etc. Examples of suitable corrosion inhibitors include long chain amines or aminodiazolines. Suitable commercially available chemicals include CronoxÔ which is a corrosion inhibitor sold by Baker Petrolite, a division of Baker-Hughes Incorporated, of Houston, Tex.

Thus, in accordance with the control and monitoring system of FIG. 9, based on information provided by the chemical sensors 500-516, corrective measures can be taken for varying the injection of the chemical (corrosion inhibitor, emulsion breakers, etc.) into the system. The injection point of these chemicals could be anywhere upstream of the location being sensed such as the location where the corrosion is being sensed. Of course, this injection point could include injections downhole. In the context of a corrosion inhibitor, the inhibitors work by forming a protective film on the metal and thereby prevent water and corrosive gases from corroding the metal surface. Other surface treatment chemicals include emulsion breakers which break the emulsion and facilitate water removal. In addition to removing or breaking emulsions, chemicals are also introduced to break out and/or remove solids, wax, etc. Typically, chemicals are introduced so as to provide what is known as a base sediment and water (B.S. and W.) of less than 1%.

In addition to the parameters relating to the chemical introduction being sensed by chemical sensors 500-516, the monitoring and control system of the present invention can also utilize known corrosion measurement devices as well including flow rate, temperature and pressure sensors. These other sensors are schematically shown in FIG. 9 at 528 and 530. The present invention thus provides a means for measuring parameters related to the introduction of chemicals into the system in real time and on line. As mentioned, these parameters include chemical concentrations and may also include such chemical properties as potential ionic content, the covalent content, pH level, oxygen levels, organic precipitates and like measurements. Similarly, oil/water cut viscosity and percent solids can be measured as well as paraffin and scale build-up, $H_2S$ content and the like. The fiber optic sensors described above may be used to determine the above mentioned parameter downhole.

Figure 10:
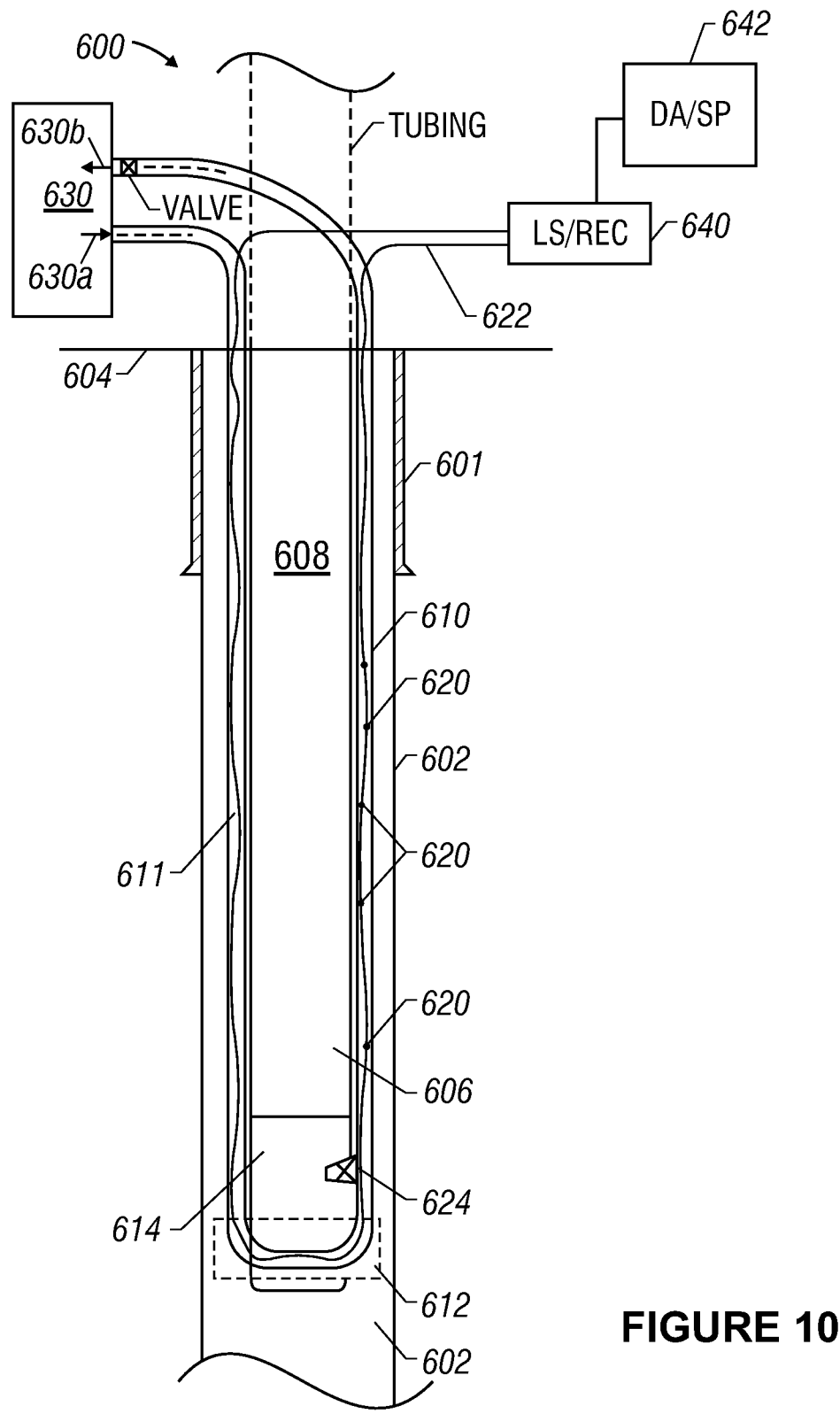
FIG. 10 is a schematic illustration of a wellbore system wherein a fluid conduit along a string placed in the wellbore is utilized for activating a hydraulically-operated device and for monitoring downhole parameters using fiber optic sensors along its length.

FIG. 10 is a schematic diagram of a wellbore system 600 wherein a common conduit is utilized for operating a downhole hydraulically-operated tool or device and for monitoring one or more downhole parameters utilizing the fiber optics. System 600 includes a wellbore 602 having a surface casing 601 installed a short distance from the surface 604. After the wellbore 102 has been drilled to a desired depth. A completion or production string 606 is conveyed into the wellbore 602. The string 606 includes at least one downhole hydraulically-operated device 614 carried by a tubing 608 which tubing may be a drill pipe, coiled tubing or production tubing. A fluid conduit 610 (or hydraulic line) having a desired inner diameter 611 is placed or attached either on the outside of the string 606 (as shown in FIG. 10) or in the inside of the string in any suitable manner. The conduit 610 is preferably routed at a desired location on the string 606 via a u-joint 612 so as to provide a smooth transition for returning the conduit 610 to the surface 604. A hydraulic connection 624 is provided from the conduit 610 to the device 614 so that a fluid under pressure can pass from the conduit 610 to the device 614.

After the string 606 has been placed or installed at a desired depth in the wellbore 602, an optical fiber 612 is pumped under pressure at the inlet 630a from a source of fluid 630. The optical fiber 622 passes through the entire length of the conduit 610 and returns to the surface 604 via outlet 630b. The fiber 622 is then optically coupled to a light source and recorder (or detector) (LS/REC) 640. A data acquisition/signal processor (DA/SP) 642 processes data/signal received via the optical fiber 622 and also controls the operation of the light source and recorder 640.

The optical fiber 622 may include a plurality of sensors 620 distributed along its length. Sensors 620 may include temperature sensors, pressure sensors, vibration sensors or any other fiber optic sensor that can be placed on the fiber optic cable 622. Sensors 620 are formed into the cable 622 during the manufacturing of the cable 622. The downhole device 614 may be any downhole fluid-activated device including but not limited to a valve, a choke, a sliding sleeve, a perforating device, and a packer, fluid flow regulation device, or any other completion and/or production device. The device 614 is activated by supplying fluid under pressure through the conduit 610. In the embodiment shown herein, the line 610 receives fiber optic cable 622 throughout its length and is connected to surface instrumentation 640 and 642 for distributed measurements of downhole parameters along its length. The line 610 may be arranged downhole along the string 606 in a V or other convenient shape. Alternatively, the line 610 may terminate at the device 614 and/or continue to a second device (not shown) downhole. the fiber optic sensors also may be disposed on the line in any other suitable manner such as wrapping them on the outside of the conduit 610. In the present invention, a common line is thus used to control a hydraulically-controlled device and to monitor one or more downhole parameters along the line.

During the completion of the wellbore 602, the sensors 620 provide useful measurements relating to their associated downhole parameters and the line 606 is used to actuate a downhole device. The sensors 620 continue to provide information about the downhole parameters over time.

Figure 11:
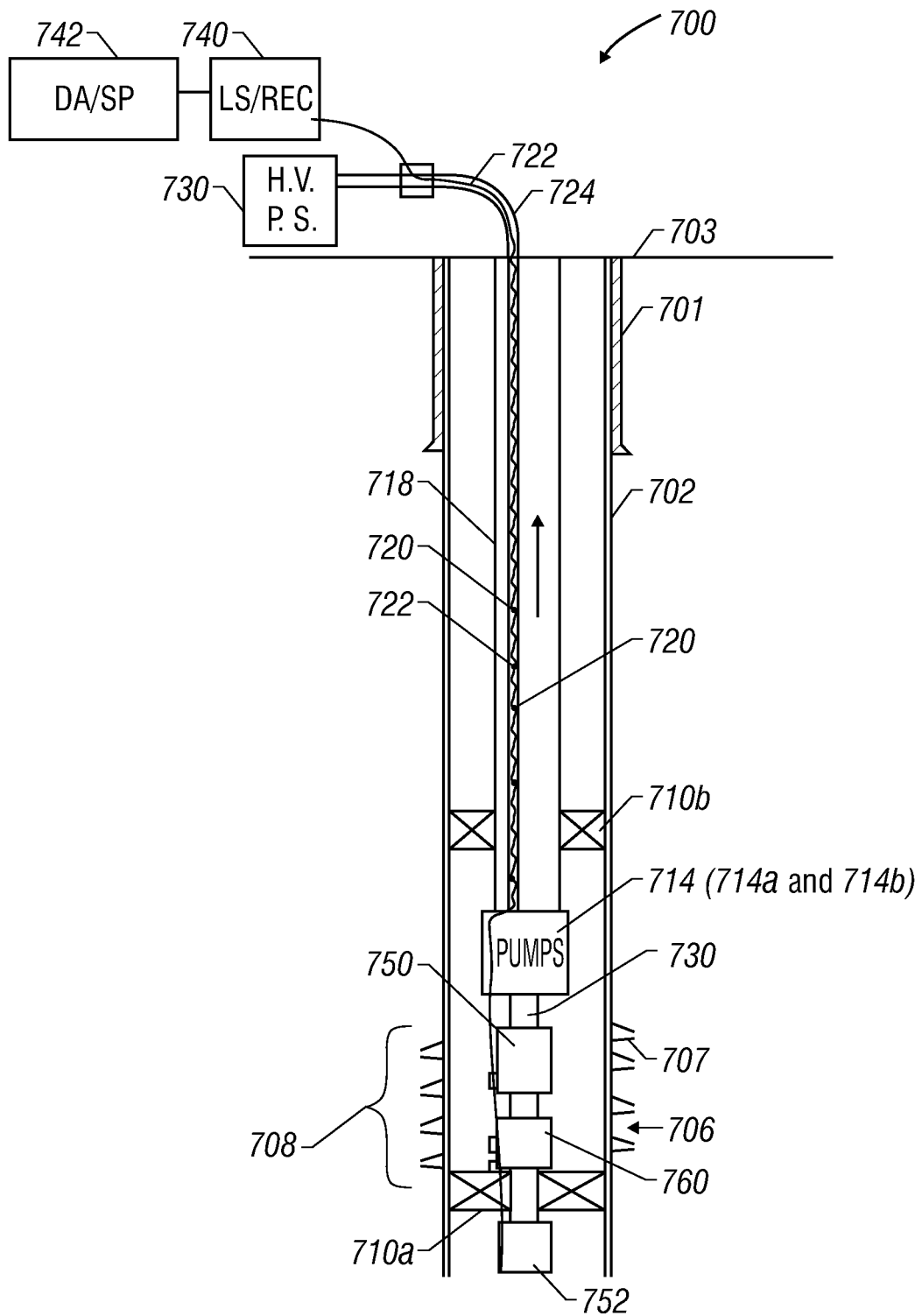
FIG. 11 shows a schematic diagram of a producing well wherein a fiber optic cable with sensors is utilized to determine the condition or health of downhole devices and to make measurements downhole relating to such devices and other downhole parameter.

FIG. 11 shows a schematic diagram of a producing well 702 that preferably has two electric submersible pumps (AESP@) 714, one for pumping the oil/gas 706 to the surface 703 and the other to pump any separated water back into a formation. The formation fluid 706 flows from a producing zone 708 into the wellbore 702 via perforations 707. Packers 710a and 710b installed below and above the ESP 714 force the fluid 706 to flow to the surface 703 via pumps ESP 714. An oil water separator 750 separates the oil and water and provide them to their respective pumps 714a-714b. A choke 752 provides desired back pressure. An instrument package 760 and pressure sensor is installed in the pump string 718 to measure related parameters during production. The present invention utilizes optical fiber with embedded sensors to provide measurements of selected parameters, such as temperature, pressure, vibration, flow rate as described below. ESP=s 714 use large amounts of electric power which is supplied from the surface via a power cable 724. Such cables often tend to corrode an/or overheated. Due to the high power being carried by the cable 724, electrical sensors are generally not placed on or along side the cable 724.

In one embodiment of the present invention as shown in FIG. 11, a fiber optic cable 722 carrying sensors 720 is placed along the power cable 724. The fiber optic cable 702 may also be extended below the ESP 714 to replace conventional sensors in the instrumentation package 760 and to provide control signals to the downhole device or processors as described earlier. In one application, the sensors 720 measure vibration and temperature of the ESP 714. It is desirable to operate the ESP at a low temperature and without excessive vibration. The ESP 714 speed is adjusted so as to maintain one or both such parameters below their predetermined maximum value or within their respective predetermined ranges. The fiber optic sensors are used in this application to continuously or periodically determine the physical condition (health) of the ESP. The fiber optic cable 722 may be extended or deployed below the ESP at the time of installing the production string 718 in the manner described with respect to FIG. 10. It should be obvious that the use of the ESP is only one example of the downhole device that can be used for the purposes of this invention. The present invention may be used to continuously measure downhole parameters, to monitor the health or condition of downhole devices and to control downhole devices. Any suitable device may be utilized for this purpose including, sliding sleeves, packers, flow control devices etc.

Figure 12:
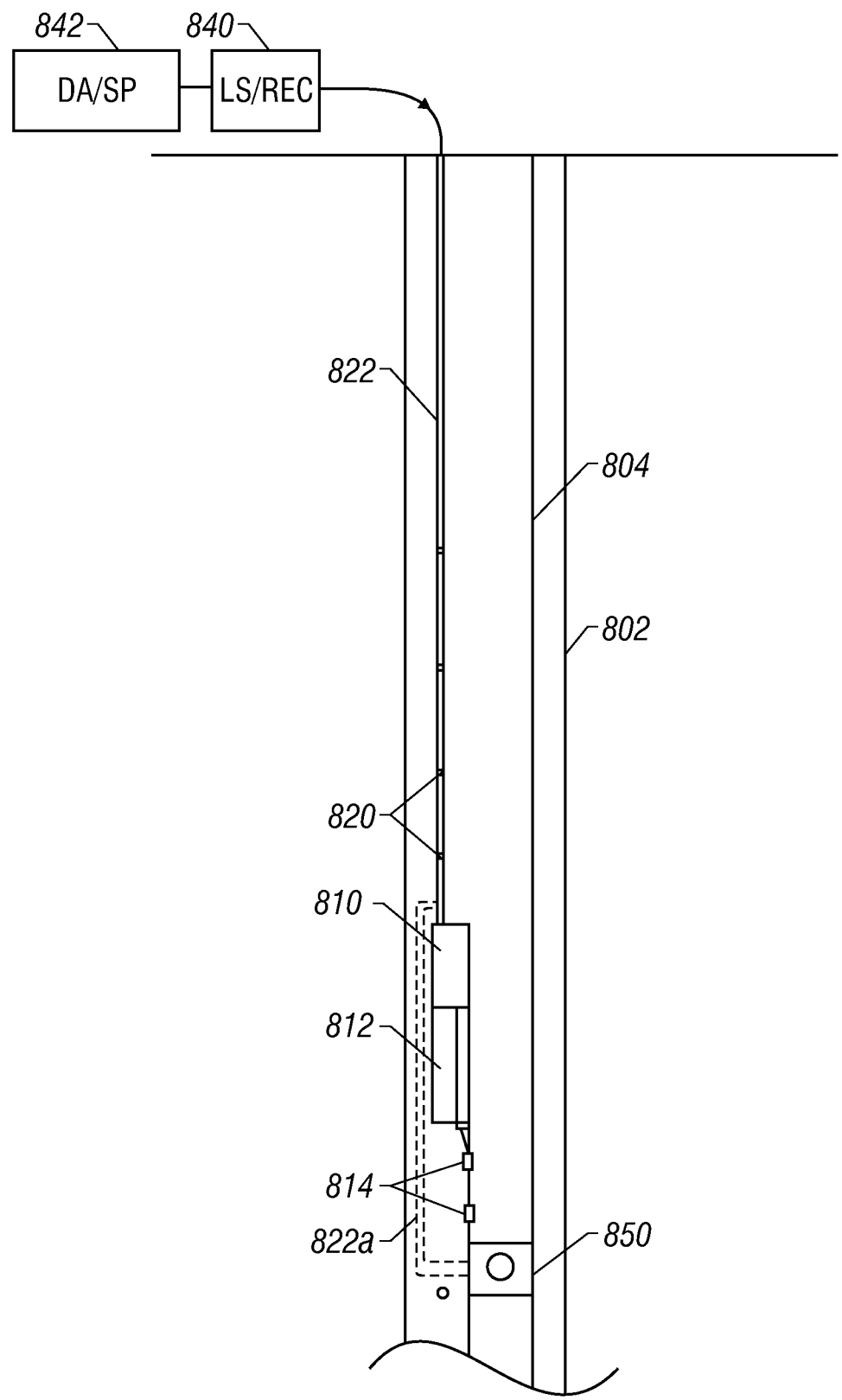
FIG. 12 is a schematic illustration of a wellbore system wherein electric power is generated downhole utilizing a light cell for use in operating sensors and devices downhole.

FIG. 12 shows a wellbore 802 with a production string 804 having one or more electrically-operated or optically-operated devices, generally denoted herein by numeral 850 and one or more downhole sensors 814. The string 804 includes batteries 812 which provide electrical power to the devices 850 and sensors 814. The batteries are charged by generating power downhole by turbines (not shown) or by supplying power from the surface via a cable (not shown).

In the present invention a light cell 810 is provided in the string 804 which is coupled to an optical fiber 822 that has one or more sensors 820 associated therewith. A light source 840 at the surface provides light to the light cell 810 which generates electricity which charges the downhole batteries 812. The light cell 810 essentially trickle charges the batteries. In many applications the downhole devices, such as devices 850, are activated infrequently. Trickle charging the batteries may be sufficient and thus may eliminate the use of other power generation devices. In applications requiring greater power consumption, the light cell may be used in conjunction with other conventional power generation devices.

Alternatively, if the device 850 is optically-activated, the fiber 822 is coupled to the device 850 as shown by the dotted line 822a and is activated by supplying optical pulses from the surface unit 810. Thus, in the configuration of FIG. 12, a fiber optics device is utilized to generate electrical energy downhole, which is then used to charge a source, such as a battery, or operate a device. The fiber 822 is also used to provide two-way communication between the DA/SP 842 and downhole sensors and devices.

Figure 13:
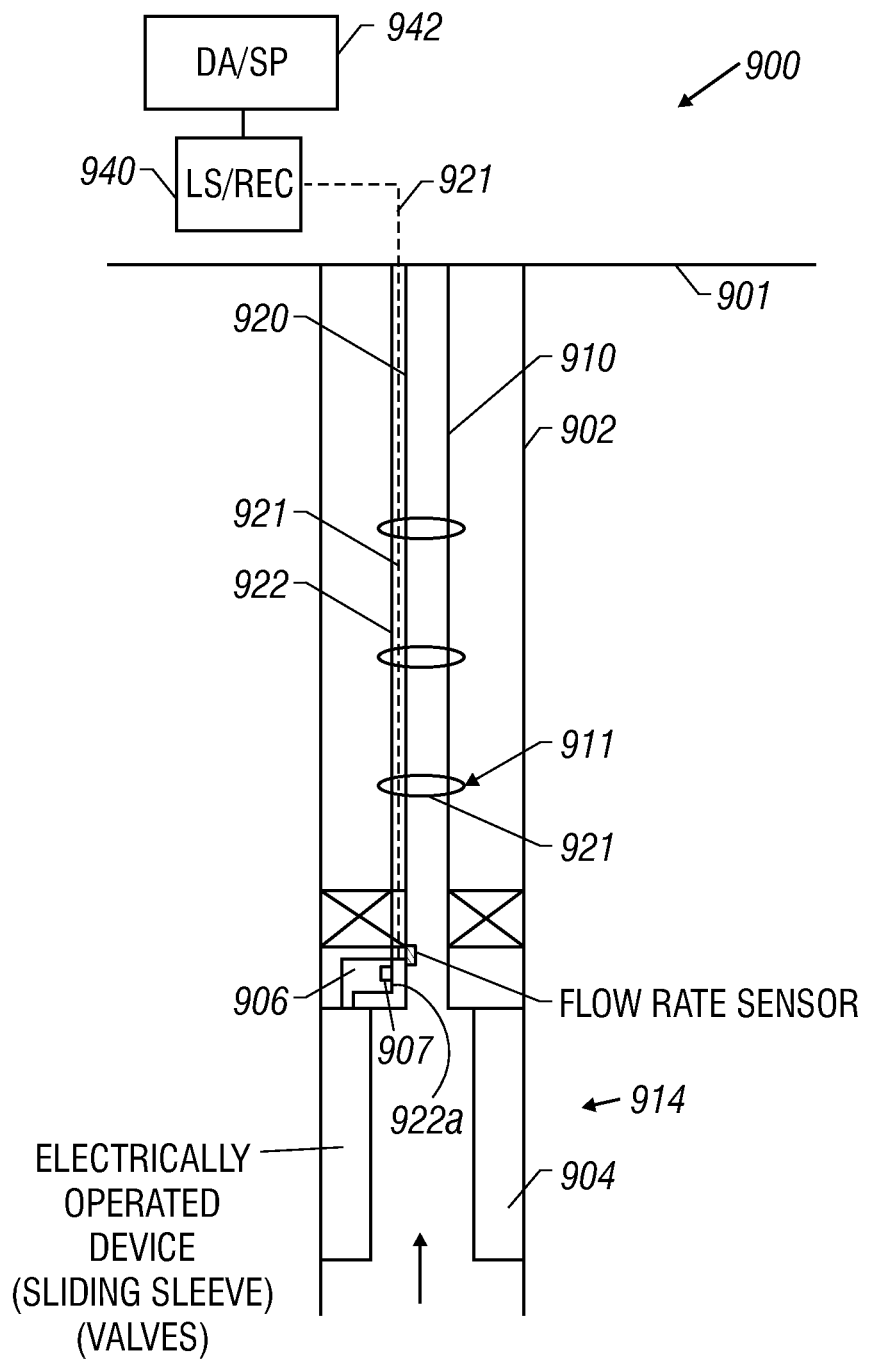
FIG. 13 is a schematic illustration of a wellbore system wherein a permanently installed electrically-operated device is monitored and operated by a fiber optic based system.

FIG. 13 shows a schematic of a wellbore system 900 wherein a permanently installed electrically-operated device is monitored and controlled by a fiber optic based system. The system 900 includes a wellbore 902 and an electrically-operated device 904 installed at a desired depth, which may be a sliding sleeve, a choke, a fluid flow control device, etc. An control unit 906 controls the operation of the device 904. A production tubing 910 installed above the device 904 allows formation fluid to flow to the surface 901. During the manufacture of the string 911 that includes the device 904 and the tubing 910, a conduit 922 is clamped along the length of the tubing 910 with clamps 921. An optical coupler 907 is provided at the electrical control unit 906 which can mate with a coupler fed through the conduit 922.

Either prior to or after placing the string 910 in the wellbore 902, a fiber optic cable 921 is deployed in the conduit 922 so that a coupler 922a at the cable 921 end would couple with the coupler 907 of the control unit 906. A light source 990 provides the light energy to the fiber 922. A plurality of sensors 920 may be deployed along the fiber 922 as described before. A sensor preferably provided on the fiber 922 determines the flow rate of formation fluid 914 flowing through the device 904. Command signals are sent by DA/SP 942 to activate the device 904 via the fiber 922. These signals are detected by the control unit 906, which in turn operate the device 904. This, in the configuration of FIG. 13, fiber optics is used to provide two way communication between downhole devices, sensors and a surface unit and to operate the downhole devices.

Figures 14A, 14B:
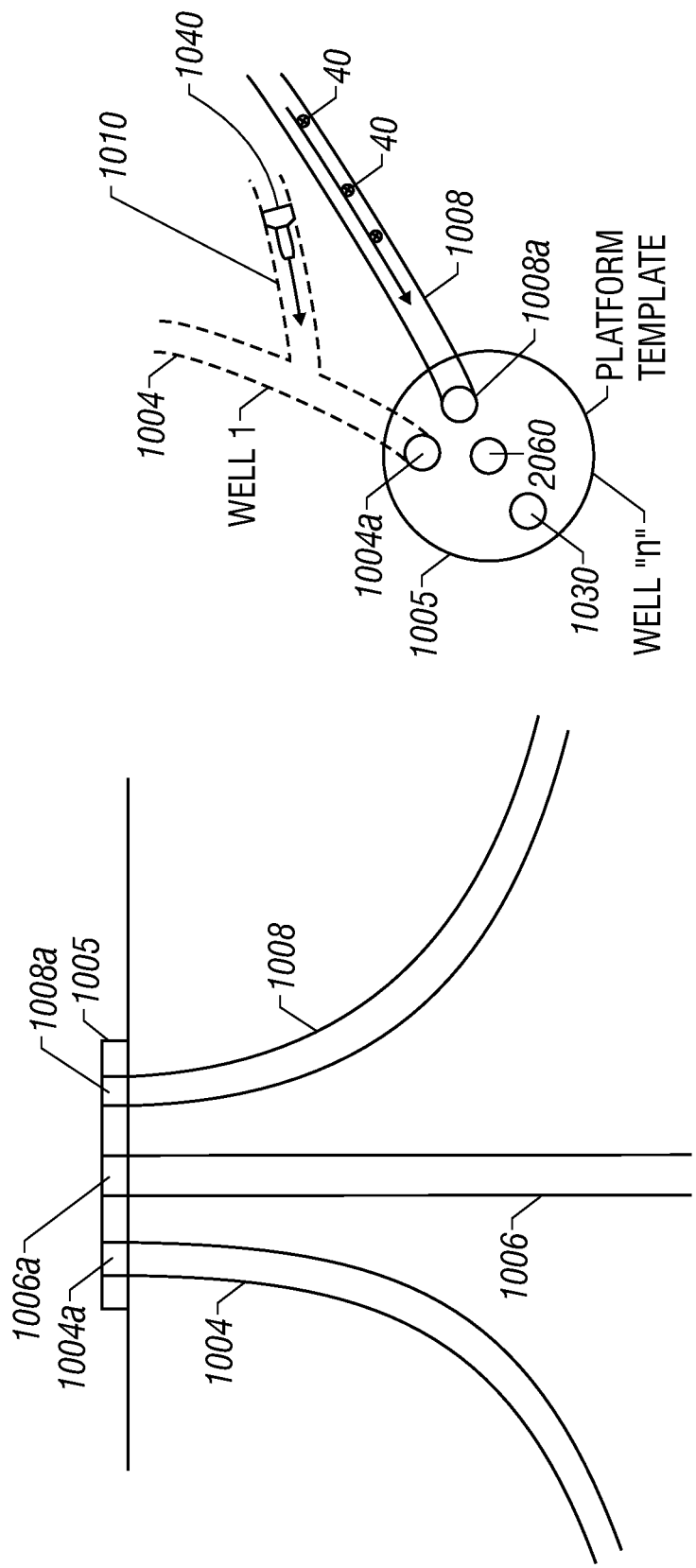
FIGS. 14A and 14B show a method to avoid drilling wellbores too close to or into each other from a common platform utilizing Fiber optic sensor in the drilling string.
Figure 14C:
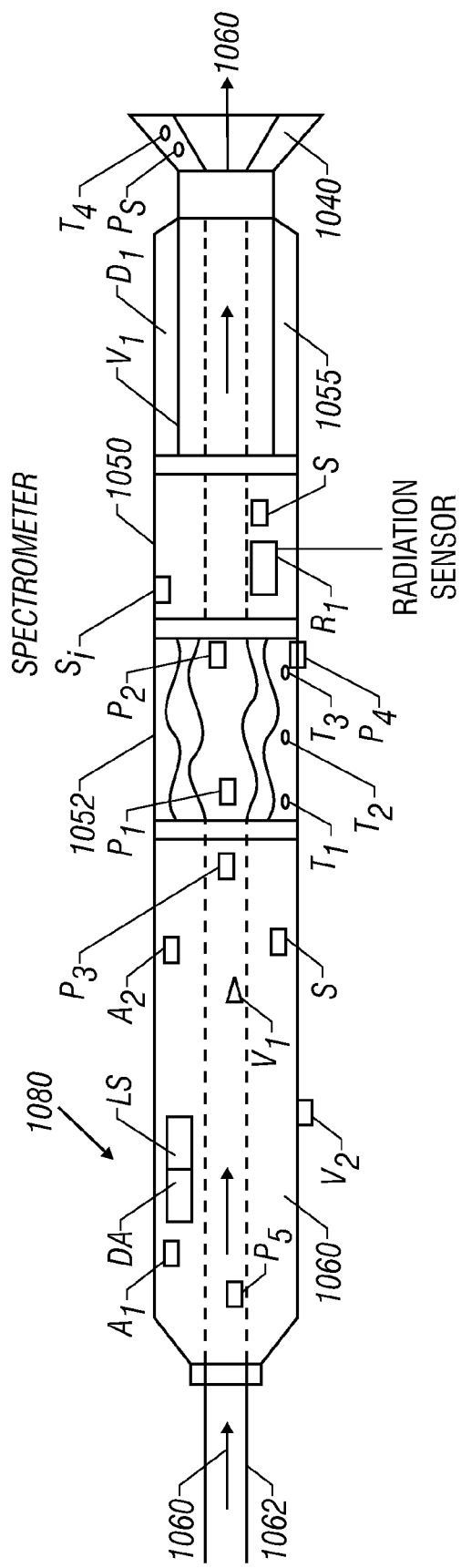

FIGS. 14A and 14B show a method monitoring the location of prior wells during drilling of a wellbore so as to avoid drilling the wellbore too close to or into the existing wellbores. Several wellbores are sometimes drilled from a rig at a single location. This is a common practice in offshore drilling because moving large platforms or rigs is not practical. Often, thirty to forty wellbores are drilled from a single location. A template is used to define the relative location of the wells at the surface. FIGS. 14A and 14B show wellbores 1004-1008 drilled from a common template 1005. The template 1005 shows openings 1004a, 1006a, and 1008a as surface locations for the wellbores 1004, 1006 and 1008 respectively. Locations of all other wellbores drilled from the template 1005 are referred to by numeral 1030. FIG. 14B also shows a lateral or branch wellbore 1010 being drilled from the wellbore 1004, by a drill bit 1040. The wellbore 1008 is presumed to be drilled before wellbores 1004 and 1010. For the purposes of this example, it is assumed that the driller wishes to avoid drilling the wellbore 1010 too close to or onto the wellbore 1008. Prior to drilling the wellbore 1010, a plurality of fiber optic sensors 40 are disposed in the wellbore 1008. The vibrations of the drill bit 1040 during drilling of the wellbore 1010 generate acoustic energy, which travels to the wellbore 1008 by a processor of the kind described earlier. The sensors 40 in the well bore 1008 detect acoustic signals received at the well bore 1008. The received signals are processed and analyzed to determine the distance of the drill bit from the wellbore 1008. The travel time of the acoustic signals from the drill bit 1040 to the sensors 40 in the wellbore 1008 provides relatively accurate measure of such distance. The fiber optic temperature sensor measurements are preferably used to correct or compensate the travel time or the underlying velocity for the effects of temperature. The driller can utilize this information to ensure that the wellbore 1010 is being drilled at a safe distance from the wellbore 1008, thereby avoiding drilling it too close or into the wellbore 1008.

The fiber optic sensors described above are especially suitable for use in drill strings utilized for drilling wellbores. For the purposes of this invention, a "drill string" includes a drilling assembly or bottom hole assembly ("BHA") carried by a tubing which may be drill pipe or coiled tubing. A drill bit is attached to the BHA which is rotated by rotating the drill pipe or by a mud motor. FIG. 15 shows a bottomhole assembly 1080 having the drill bit 1040 at one end. The bottomhole assembly 1080 is conveyed by a tubing 1062 such as a drill pipe or a coiled-tubing. A mud motor 1052 drives the drill bit 1040 attached to the bottom hole end of the BHA. A bearing assembly 1055 coupled to the drill bit 1040 provides lateral and axial support to the drill bit 1040. Drilling fluid 1060 passes through the drilling assembly 1080 and drives the mud motor 1052, which in turn rotates the drill bit 1040.

As described below, a variety of fiber optic sensors are placed in the BHA 1080, drill bit 1040 and the tubing 1082. Temperature and pressure sensors T4 and P5 are placed in the drill bit for monitoring the condition of the drill bit 1040. Vibration and displacement sensors V1 monitor the vibration of the BHA and displacement sensors V1 monitor the lateral and axial displacement of the drill shaft and that of the BHA. Sensors T1-T3 monitor the temperature of the elastomeric stator of the mud motor 1052, while the sensors P1-P4 monitor differential pressure across the mud motor, pressure of the annulus and the pressure of the fluid flowing through the BHA. Sensors V1-V2 provide measurements for the fluid flow through the BHA and the wellbore. Additionally a spectrometric sensors S1 of the type described above may be placed in a suitable section 1050 of the BHA to measure the fluid and chemical properties of the wellbore fluid. Fiber optic sensor R1 is used to detect radiation. Acoustic sensors S1-S2 may be placed in the BHA for determining the acoustic properties of the formation. Additionally sensors, generally denoted herein as S may be used to provide measurements for resistivity, electric field, magnetic field and other measurements that can be made by the fiber optic sensors. A light source LS and the data acquisition and processing unit DA are preferably disposed in the BHA. The processing of the signals is preferably done downhole, but may be done at the surface. Any suitable two way communication method may be used to communicate between the BHA and the surface equipment, including optical fibers. The measurements made are utilized for determining formation parameters of the kind described earlier, fluid properties and the condition of the various components of the drill string including the condition of the drill bit, mud motor, bearing assembly and any other component part of the drilling assembly.

While foregoing disclosure is directed to the preferred embodiments of the invention, various modifications will be apparent to those skilled in the art. It is intended that all variations within the scope and spirit of the appended claims be embraced by the foregoing disclosure.

What is claimed is:

1. A method of monitoring and controlling an injection operation, comprising:
    locating in a production well a plurality of distributed fiber optic sensors;
    injecting a fluid in an injection well formed spaced apart from the production well;
    determining a parameter of the formation between the production well and the injection well from a measurement of an acoustic signal generated in the formation obtained using the fiber optic sensors; and
    controlling a flow of fluid into the production well in response to the parameter determined from the measurement of the acoustic signal generated in the formation.

2. The method of claim 1 wherein the fiber optic sensors comprise strain sensors and the determined parameter comprises a depletion of hydrocarbons.

3. The method of claim 2 further comprising estimating a stress distribution at the production well.

4. The method of claim 1 wherein the fiber optic sensors comprise acoustic sensors and the determined parameter comprises at least one of: (i) a seismic map, (ii) an extent of fracturing of the formation, and (iii) a sealing character of a fault.

5. The method of claim 4 further comprising using a seismic source at a surface location to generate acoustic waves in the formation.

6. The method of claim 4 further comprising using a seismic source in the injection well to generate an acoustic wave in the formation.

7. The method of claim 1 further comprising using a flow controller for controlling at least one of: (i) the injection of fluid, and (ii) the flow into the production well.

8. A system configured to monitor and control an injection operation, the system comprising:
    an injection well spaced apart from a production well, the injection well configured to have a device for injecting a fluid into the formation;
    a plurality of fiber optic sensors disposed in a production well, the fiber optic sensors configured to measure an acoustic signal generated in the formation in response to the injection of the fluid; and
    at least one processor configured to:
    (i) determine from the measured acoustic signal a parameter of the formation between the production well and the injection well; and
    (ii) control a flow into the production well in response to the parameter determined from the measured acoustic signal.

9. The system of claim 8 wherein the fiber optic sensors comprise strain sensors and the parameter determined by the at least one processor further comprises a depletion of hydrocarbons.

10. The system of claim 8 wherein the at least one processor is further configured to estimate a stress distribution at the production well.

11. The system of claim 8 wherein the fiber optic sensors comprise acoustic sensors and the parameter determined by the at least one processor further comprises at least one of: (i) a seismic map, (ii) an extent of fracturing of the formation, and (iii) a sealing character of a fault.

12. The system of claim 11 further comprising a seismic source at a surface location configured to generate acoustic waves in the formation.

13. The system of claim 11 further comprising a seismic source in the injection well configured to generate an acoustic wave in the formation.

14. The system of claim 8 further comprising a flow controller configured to control at least one of: (i) the injection of fluid, and (ii) the flow into the production well.

\* \* \* \* \*